United States Patent
Bocchi et al.

(10) Patent No.: US 10,569,270 B2
(45) Date of Patent: Feb. 25, 2020

(54) SCREENING KIT AND METHOD

(71) Applicant: CELLPLY S.R.L., Bologna (IT)

(72) Inventors: Massimo Bocchi, Sasso Marconi (IT); Andrea Faenza, Bologna (IT); Laura Rocchi, Bologna (IT); Dario Biscarini, Bologna (IT); Nicola Pecorari, Bologna (IT)

(73) Assignee: CELLPLY S.R.L., Bologna (IT)

( * ) Notice: Subject to any disclaimer, the term of this patent is extended or adjusted under 35 U.S.C. 154(b) by 0 days.

(21) Appl. No.: 15/623,149

(22) Filed: Jun. 14, 2017

(65) Prior Publication Data

US 2018/0043357 A1 Feb. 15, 2018

(30) Foreign Application Priority Data

Jun. 14, 2016 (IT) .......................... 102016000061106
Dec. 1, 2016 (IT) .......................... 102016000122158

(51) Int. Cl.

| | |
|---|---|
| *G01N 33/50* | (2006.01) |
| *B01L 3/00* | (2006.01) |
| *B01L 3/02* | (2006.01) |
| *G01N 35/10* | (2006.01) |
| *G01N 15/14* | (2006.01) |
| *G06K 9/00* | (2006.01) |
| *G01N 1/30* | (2006.01) |
| *G01N 1/31* | (2006.01) |
| *G06T 7/00* | (2017.01) |
| *G01N 15/10* | (2006.01) |

(52) U.S. Cl.
CPC ......... *B01L 3/50273* (2013.01); *B01L 3/0275* (2013.01); *B01L 3/502715* (2013.01); *G01N 1/30* (2013.01); *G01N 1/31* (2013.01); *G01N 15/1463* (2013.01); *G01N 15/1484* (2013.01); *G01N 33/5011* (2013.01); *G01N 35/10* (2013.01); *G01N 35/1011* (2013.01); *G06K 9/00147* (2013.01); *G06T 7/0012* (2013.01); *B01L 2200/027* (2013.01); *B01L 2200/0689* (2013.01); *B01L 2300/06* (2013.01); *B01L 2300/0609* (2013.01); *B01L 2300/0816* (2013.01); *B01L 2300/0832* (2013.01); *B01L 2300/0861* (2013.01); *B01L 2400/04* (2013.01); *B01L 2400/0406* (2013.01); *B01L 2400/0487* (2013.01); *G01N 2015/1006* (2013.01); *G01N 2015/1493* (2013.01); *G01N 2015/1497* (2013.01); *G01N 2500/10* (2013.01); *G06T 7/0014* (2013.01); *G06T 2207/10056* (2013.01); *G06T 2207/30024* (2013.01); *G06T 2207/30072* (2013.01); *G06T 2207/30242* (2013.01)

(58) Field of Classification Search
CPC ............... B01L 3/50273; B01L 3/0275; B01L 3/502715; B01L 2200/027; B01L 2200/0689; B01L 2300/0816; B01L 2300/06; B01L 2300/0609; B01L 2300/0832; B01L 2300/0861; B01L 2400/04; B01L 2400/0406; B01L 2400/0487; G01N 1/30; G01N 1/31; G01N 35/1011; G01N 15/1463; G01N 15/1484; G01N 33/5011; G01N 35/10; G01N 2015/1006; G01N 2015/1493; G01N 2015/1497; G01N 2500/10; G06T 7/0012; G06T 2207/30242; G06T 7/0014; G06T 2207/10056; G06T 2207/30024; G06T 2207/30072; G06K 9/00147

See application file for complete search history.

(56) References Cited

U.S. PATENT DOCUMENTS

| | | | |
|---|---|---|---|
| 4,747,919 | A | 5/1988 | Anderson |
| 5,496,697 | A | 3/1996 | Parce et al. |
| 5,589,047 | A | 12/1996 | Coster et al. |
| 5,814,668 | A | 9/1998 | Whittemore et al. |
| 5,846,396 | A | 12/1998 | Zanzucchi et al. |
| 6,610,188 | B1 | 8/2003 | Fuhr et al. |
| 6,652,809 | B1 | 11/2003 | Comley et al. |

(Continued)

FOREIGN PATENT DOCUMENTS

| | | |
|---|---|---|
| CN | 101460253 A | 6/2009 |
| EP | 1088592 A2 | 4/2001 |

(Continued)

OTHER PUBLICATIONS

Park, Min Cheol; et al. "High-Throughput Single-Cell Quantification Using Simple Microwell-Based Cell Docking and Programmable Time-Course Live-Cell Imaging." Lab Chip, 11:79-86, 2011.

(Continued)

*Primary Examiner* — Julie Wu
*Assistant Examiner* — Carmencita M Belei
(74) *Attorney, Agent, or Firm* — Meunier Carlin & Curfman LLC

(57) ABSTRACT

Methods are provided for the large-scale high-content analysis of biological samples. In some embodiments, the methods are implemented in a reversed open microwell system that includes an array of open microwells, at least one microchannel, at least one input port and at least one output port. In certain embodiments, the reversed open microwell system can be inserted in an automated management system which includes an incubator at controlled temperature, humidity and CO2 levels, a fluid dispensing system, and is capable of phase-contrast and fluorescence image acquisition.

Also provided are kits for introducing fluids into a microfluidic device, and systems for discharging one or more fluids in a microfluidic device.

9 Claims, 25 Drawing Sheets

(56) References Cited

U.S. PATENT DOCUMENTS

| | | | |
|---|---|---|---|
| 6,716,629 B2 | 4/2004 | Hess et al. |
| 6,932,893 B2 | 8/2005 | Bech et al. |
| 6,942,776 B2 | 9/2005 | Medoro |
| 7,018,819 B2 | 3/2006 | Orwar et al. |
| 7,081,189 B2 | 7/2006 | Squires et al. |
| 7,189,578 B1 | 3/2007 | Feng et al. |
| 7,238,268 B2 | 7/2007 | Ramsey et al. |
| 7,776,553 B2 | 8/2010 | Love et al. |
| 8,388,823 B2 | 3/2013 | Manaresi et al. |
| 9,039,883 B2 | 5/2015 | Guerrieri et al. |
| 9,816,910 B2 | 11/2017 | Bocchi et al. |
| 2002/0036139 A1 | 3/2002 | Becker et al. |
| 2002/0053399 A1 | 5/2002 | Soane et al. |
| 2002/0092767 A1 | 7/2002 | Bjornson et al. |
| 2002/0125139 A1 | 9/2002 | Chow et al. |
| 2002/0142482 A1 | 10/2002 | Wu et al. |
| 2002/0182627 A1 | 12/2002 | Wang et al. |
| 2002/0182657 A1 | 12/2002 | Ranger |
| 2002/0182749 A1 | 12/2002 | Singh et al. |
| 2003/0039585 A1 | 2/2003 | Freeman |
| 2003/0087309 A1 | 5/2003 | Chen |
| 2003/0104588 A1 | 6/2003 | Orwar et al. |
| 2004/0011652 A1 | 1/2004 | Bressler |
| 2004/0175708 A1 | 9/2004 | Caillat et al. |
| 2005/0058990 A1 | 3/2005 | Guia et al. |
| 2005/0139473 A1 | 6/2005 | Washizu et al. |
| 2006/0029955 A1 | 2/2006 | Guia et al. |
| 2006/0196772 A1 | 9/2006 | Kim et al. |
| 2006/0199173 A1 | 9/2006 | Thielecke et al. |
| 2006/0231405 A1 | 10/2006 | Hughes et al. |
| 2007/0243523 A1 | 10/2007 | Ionescu-Zanetti et al. |
| 2008/0067068 A1 | 3/2008 | Li |
| 2008/0210558 A1 | 9/2008 | Sauter-Starace et al. |
| 2009/0107907 A1 | 4/2009 | Chen et al. |
| 2009/0258383 A1 | 10/2009 | Kovac et al. |
| 2009/0288963 A1 | 11/2009 | Guerrieri et al. |
| 2010/0152054 A1 | 6/2010 | Love et al. |
| 2012/0034623 A1 | 2/2012 | Hulsken et al. |
| 2013/0068618 A1 | 3/2013 | Harrer et al. |
| 2013/0134040 A1 | 5/2013 | Lee et al. |
| 2013/0252258 A1 | 9/2013 | Bocchi et al. |
| 2013/0256137 A1 | 10/2013 | Holt |
| 2013/0261021 A1 | 10/2013 | Bocchi et al. |
| 2015/0209786 A1 | 7/2015 | Hage et al. |
| 2016/0161392 A1 | 6/2016 | Ionescu-Zanetti et al. |
| 2016/0178502 A1 | 6/2016 | Bocchi et al. |

FOREIGN PATENT DOCUMENTS

| | | | |
|---|---|---|---|
| EP | 1185373 B1 | 3/2002 |
| EP | 1390467 B1 | 2/2004 |
| WO | WO199962622 A1 | 9/1999 |
| WO | 1999062622 A1 | 12/1999 |
| WO | WO2001009297 A1 | 2/2001 |
| WO | 2002088300 A1 | 11/2002 |
| WO | WO2007138464 A2 | 12/2007 |
| WO | WO2009151505 A1 | 12/2009 |
| WO | 2010085275 A1 | 7/2010 |
| WO | 2010135468 A1 | 11/2010 |
| WO | WO2012072822 A1 | 6/2012 |
| WO | WO2012072823 A1 | 6/2012 |

OTHER PUBLICATIONS

International Search Report and Written Opinion issued in PCT/EP2011/071820, dated Mar. 30, 2012, 11 pages.
"Apoptosis, Cell Death, and Cell Proliferation—3rd Edition," Roche Applied Science, Aug. 2004, 174pp.
Anderson, Melvin, et al. "Recent Advances in 2D and 3D in Vitro Systems Using Primary Hepatocytes, Alternative Hepatocyte Sources and Non-Parenchymal Liver Cells and Their Use in Investigating Mechanisms of Hepatotoxicity, Cell Signaling and ADME." Arch. Toxicol., Review Article, 87:1315-1530, 2013.
Au, Anthony K., et al. "Review: Microvalves and Micropumps for BioMEMS." Micromachines, 2:179-220, 2011.
Bernards, Rene and Van't Veer, Laura J. "Enabling Personalized Cancer Medicine Through Analysis of Gene-Expression Patterns." Nature, 452(3):564-570, May 2008.
Bessette, Paul H., et al., "Microfluidic Library Screening for Mapping Antibody Epitopes," Analytical Chemistry, vol. 79, No. 5, Mar. 1, 2007, pp. 2174-2178, XP55022596.
Bhat, Rauf et al., "Serial Killing of Tumor Cells by Human Natural Killer Cells—Enhancement by Therapeutic Antibodies", PLOS One, vol. 2, No. 3, 2007, e326, 7 pages.
Bocchi et al. "Dielectrophoretic trapping in microwells for manipulation of single cells and small aggregates of particles" Biosensors and Bioelectronics 24 (2009) 1177-1183.
Bocchi et al. "Inverted open microwells for analysis and functional sorting of single live cells" 15th International Conference on Miniaturized Systems for Chemistry and Life Sciences Oct. 2-6, 2011, Seattle, Washington, USA.
Bocchi et al. "Inverted open microwells for cell trapping, cell aggregate formation and parallel recovery of live cells" Lab Chip, 2012, 12, 3168-3176.
Bocchi, Massimo et al., "Electronic Microsystems for Handling of Rare Cells," IEEE Transactions on Electron Devices, vol. 57, No. 1, Jan. 1, 2010, pp. 244-255.
Dai, MingHua and Copley, Shelley D. Genome Shuffling Improves Degradation of the Anthropogenic Pesticide Pentachlorophenol by Sphingobium Chlorophenolicum ATCC 39723. Applied and Environmental Microbiology, 70(4):2391-2397, Apr. 2004.
Duqi, E. et al., "Automated isolation of a programmable numbers of cells into microwells using DEP forces and optical detection", International Conference on Microtechnologies in Medicine and Biology, May 2011, 2 pages.
Dura et al. "Spatially and temporally controlled immune cell interactions using microscale tools" Current Opinion in Immunology 2015, 35:23-29.
El-Ali, Jamil et al. "Cells on Chips." Nature, vol. 442, Jul. 27, 2006. 9 pages.
Fabian, Ina and Kravtsov, Vladimir D. "Automated Monitoring of Apoptosis in Suspension Cell Cultures." Laboratory Investigation, 74(2):557-570, 1996.
Faenza et al. "Impedance measurement technique for high-sensitivity cell detection in microstructures with non-uniform conductivity distribution" Lab Chip, 2012, 12, 2046-2052.
Faenza, A. et al., "Controlled isolation and patterning of K562 leukemia cells using electrically activated microchannels", International Conference on Microtechnologies in Medicine and Biology, May 2011.
Faenza, Andrea et al., "Continuous Impedance Monitoring of Single Cells Delivered in Open Microwell Arrays", presented at the 13th International Conference on Miniaturized Systems for Chemistry and Life Sciences, Nov. 1-5, 2009, Jeju, Korea, 3 pages.
Han et al., "Integration of single oocyte trapping, in vitro fertilization and embryo culture in a microwell-structured microfluidic device", Lab on a Chip, vol. 10, No. 21, 2010, pp. 2848-2854.
Higashiyama, Kenichi et al. "Dielectric Analysis for Estimation of Oil Content in the Mycelia of Mortierella Alpina." Biotechnology and Bioengineering, vol. 65, No. 5, Dec. 5, 1999. 6 pages.
International Search Report and Written Opinion issued in Italian Application No. 102016000061106, dated Feb. 9, 2017, 10 pages, including English translation of Written Opinion.
International Search Report and Written Opinion issued in PCT/EP2011/071819, dated May 4, 2012, 14 pages.
International Search Report and Written Opinion issued in PCT/IB2007/001427, completed Nov. 13, 2007, 7 pages.
Jin, Aishun et al., "A rapid and efficient single-cell manipulation method for screening antigen-specific antibody-secreting cells from human peripheral blood" Nature Medicine, vol. 15, 2009, pp. 1088-1092.
Khine, Michelle, et al. "A Single Cell Electroporation Chip." The Royal Society of Chemistry, Lab on a Chip, vol. 5:38-43, 2005.

(56) References Cited

OTHER PUBLICATIONS

Konry et al. "Droplet-based microfluidic platforms for single T cell secretion analysis of IL-10 cytokine" Biosens Bioelectron. Jan. 15, 2011; 26(5): 2707-2710. Published online Sep. 15, 2010 doi:10.1016/j.bios.2010.09.006).

Lin, Yu-Cheng, et al. "A Microchip for Electroporation of Primary Endothelial Cells." Sensors and Actuators A 108:12-19, 2003.

Love, Christopher J. et al., "A Microengraving Method for Rapid Selection of Signal Cells Producing Antigen-Specific Antibodies", Nature Biotechnology, Jun. 2006, vol. 24 No. 6, 6 pages.

Lucas, et al. "Lab-on-a-chip Immunoassay for Multiple Antibodies Using Microsphere Light Scattering and Quantum Dot Emission," Biosensors and Bioelectronics, Elsevier BV, NL, vol. 23, No. 5, Nov. 15, 2007, pp. 675-681, XP022345923.

Majumder, Biswanath, et al. "Predicting Clinical Response to Anticancer Drugs Using an Ex Vivo Platform That Captures Tumour Heterogeneity." Nature Communications, 6:6169, Feb. 27, 2015, pp. 1-14.

Matsudaira, Paul. "Intrahelical Ion Pairs in Intermediate Filaments." Proc. Natl. Acad. Sci. USA, Commentary, vol. 92, p. 86, Jan. 1995.

Muller, Torsten et al. "The Potential of Dielectrophoresis for Single-Cell Experiments." IEEE Engineering in Medicine and Biology Magazine. Nov./Dec. 2003. 12 pages.

Neri, Simona et al., "Calcein-Acetyoxymethyl Cytotoxicity Assay: Standardization of a Method Allowing Additional Analyses on Recovered Effector Cells and Supermatants", Clinical and Diagnostic Laboratory Immunology, Nov. 2011, vol. 8, No. 6 pp. 1131-1135.

Rastogi, Vinayak, et al., "Development and Evaluation of Realistic Microbiosassays in Freely Suspended Dropletson a Chip," Biomicrofluids, AIP, US, Online, vol. 1, No. 1, Mar. 1, 2007, pp. 14107-1, XP008149939.

Ronan, J.L. et al., "Optimization of the surfaces used to capture antibodies from single hybridomas reduces the time required for microengraving" J. Immunol. Methods, vol. 340, No. 2, Jan. 2009, pp. 164-169.

Salter, Russel D. and Cresswell, Peter. "Impaired Assembly and Transport of HLA-A and -B Antigens in a Mutant TxB Cell Hybrid." The EMBO Journal, 5(5): 943-949, 1986.

Sohn, L. L., et al. "Capacitance Cytometry: Measuring Biological Cells One by One." PNAS, 97(20):10687-10690, Sep. 26, 2000.

Staunton, Jane E., et al. "Chemosensitivity Prediction by Transcriptional Profiling." PNAS, 98(19):10787-10792, Sep. 11, 2001.

Stromberg, Anette et al. "Microfluidic Device for Combinatorial Fusion of Liposomes and Cells." Analytical Chemistry, vol. 73, No. 1, Jan. 1, 2001. 6 pages.

Thielecke, Hagen, et al. "A Multicellular Spheroid-Based Sensor for Anti-Cancer Therapeutics." Biosensors & Electronics, 16:261-269, 2001.

Tian, C., et al. "Evaluation of a Chemoresponse Assay as a Predictive Marker in the Treatment of Recurrent Ovarian Cancer: Further Analysis of a Propsective Study." British Journal of Cancer, 111:843-850, 2014.

Weisenthal, Larry M. "A Novel Dye Exclusion Method for Testing in Vitro Chemosensitivity of Human Tumors." Cancer Research, 43:749-757, Feb. 1983.

SCREENING KIT AND METHOD

BACKGROUND ART

With the progress of knowledge related to genomics, the need to move from a treatment generally applicable to a given disease to a treatment specifically applicable to a specific individual affected by the such a disease is increasingly felt in medicine. The advantages of a customized therapeutic approach are apparent, where an inadequate selection of patients to be treated leads to a health expenditure which may be contained not only by being able to predict, and thus avoid, often expensive and ineffective treatments for the specific subject but also avoiding adverse patient-specific effects.

In tumor therapy, this need is particularly felt, where the effectiveness of treatments is typically low: even drugs aimed at specific genetic mutations may be ineffective in 80-90% of cases in the absence of an adequate selection of patients (B Majumder et al., Predicting clinical response to anticancer drugs using an ex vivo platform which captures tumour heterogeneity. Nat. Commun. 2015, 6:6169).

With the aim of being able to achieve tests which enable the effective implementation of customized medicine, tests have been successfully developed which are based on the genetic profile and on protein expression (Staunton J E et al, Chemosensitivity predicition by transcriptional profiling. PNAS 2001, 98:10787-10792; van't Veerand L J, Bernarnds R, Enabling personalised cancer medicine through analysis of gene-expression patterns. Nature 2008, 452:564-570). However, especially in tumors, the relevance of the tumor microenvironment in conjunction with other characteristics of the patient to determine the effectiveness of a therapy has been widely demonstrated. To take also these factors into due consideration, the need for ex vivo functional assays is strongly felt (Tan C. et al., Evaluation of a chemoresponse assay as a predictive marker for the treatment of recurrent ovarian cancer: further analysis of a prospective study. British J. Cancer 2014, 111:843-850).

Ex-vivo functional assays are currently available which, where implemented by carrying out the analysis immediately downstream of the biological sample collection and maintaining said sample under controlled conditions and as much as possible similar to those representative of the tumor microenvironment in-vivo, have demonstrated a high ability to predict the efficacy of drug therapies. As an example, a method is described in WO2010/135468. However, the ex-vivo functional assays available to date exhibit important limitations.

In particular, the assays developed for the ex-vivo analysis of the pharmacological activity in hematology and oncology are mainly based on the use of flow cytometry (FACS) and/or fluorimetric or colorimetric assays involving kits used to measure the cell viability and/or proliferation on whole cell populations, such as the metabolic assays MTT, ATP, the MiCK assay (Kravtsov V D & Fabian's Automated monitoring of apoptosis in cell suspension cultures. Lab. Invest. 1996, 74:551-570) and the DiSC assay (Weisenthal L M et al., A novel dye exclusion method for testing in vitro chemosensitivity of human tumors. Cancer Res. 1983, 43:749-757) for measuring ell death and apoptosis. Such assays inevitably have several limitations. Flow cytometry, for example, exhibits the inability to obtain high-content analyses in time-lapse and the inability to work on cell aggregates, as the cellular breakdown is a fundamental prerequisite for running the test, thereby preventing the evaluation of the response of a cell in its context. The techniques which provide a measure on whole populations are generally characterized by the difficulty of carrying out an analysis limited to the tumor subpopulation and are therefore of limited accuracy. In addition, in all the techniques described, the required sample volumes are typically significant and not always compatible with the clinical practice. For example, in order to reduce the invasiveness of the sampling procedures or in the presence of tumors of limited size, such as metastasis, the sample is available in small quantities, for example up to a few thousands cells or a few dozen cells, if the sample comes from a liquid biopsy, i.e. by the isolation of circulating tumor cells, insufficient quantities to be analyzed according to the techniques described. Having a biological sample which comprises between a few thousands cells and a few dozen cells, conducting a cell analysis on such a sample is difficult to implement through the currently existing instruments and, when it can be implemented, the analysis is still limited to one or very few experimental conditions per sample. In even more complex cases in which only a few cells, such as 10-20 cells, are available, no significant data can be obtained using the functional assays currently available. Moreover, functional assays are currently typically carried out by operators who require specialized laboratories, with expertise and equipment which are not easily accessible. The analysis platforms based on flow cytometry, if provided with complete automation, are represented by complex and bulky machinery, therefore hardly adoptable in clinical contexts and, more particularly, in diagnostic laboratories. Likewise, other techniques described require manual performance of the operations and the availability for an entire laboratory to carry out the diagnostic testing. The tests are then carried out in laboratories far from the place of sampling, thereby delaying the start of the test by a few days, often making them not compatible with the timing of clinical practice, which may need the results within 24-48 hours.

WO2012/072822 describes a system with microwells open upwards and downwards, where channels put said microwells in fluidic communication and the geometry of said microwells allows the formation of a meniscus within them on which the cells and/or particles introduced into the same rest. Optionally, said microwells comprise electrodes which allow to control the movements of cells and/or particles into the same microwells.

US2016/161392

The need is strongly felt for a functional assay based on cell analysis capable of giving answers in a short time since obtaining the biological sample, for example within 24-48 hours, and which allows to obtain high-content data on the cells analyzed, i.e. inclusive of morphological information, even in time-lapse, allowing the dynamic analysis of the information detected on the cells in the sample. Moreover, said assay should be as operator-independent as possible and require small volumes of biological sample, so as to also limit the volumes of reagents and drugs to be used in the execution thereof, thus containing costs, maintaining the ability to provide reliable results even with very small biological samples in terms of quantity, such as also having just 20 cells.

The movement of fluids in microfluidic devices typically uses vacuum or pressure pumps and/or valves. The combination of pumps and valves allows a fine control of the movements of fluids in a circuit.

By way of example, Byun et al. (Pumps for Microfluidic Cell Cultures, Electrophoresis 2014, 35:245-257) describe microfluidic devices for cell culture and pumping systems associated therewith. Also Au et al. (Microvalves and micropumps for BioMEM, Micromachines 2011, 2:179-220) describe a wide variety of valves and pumps to be used in specific combinations, each with unique features which make it applicable in certain contexts and not in others.

The available literature shows that there are no standard parameters on which the selection of micro-pumps and micro-valves should be based, thus requiring a specific study for each specific system.

A strongly felt problem is to efficiently manage the bi-directional movement of fluids in a microcircuit, without necessarily having to rely on pumps and valves, which are bulky and demanding from the point of view of purchase and management costs.

A further problem associated with the microfluidic devices based on valves is that, if the integration of valves in the microsystem is contemplated to obtain high parallelism and/or reduced overall dimensions, the technological complexity required is high, for example due to the need of integrating elastomers as well as rigid materials.

The present invention offers a simple and advantageous solution to the problem by allowing the use of a common liquid handling instrument for the high precision charging, pumping and optionally discharging of fluids in a microfluidic device.

DESCRIPTION OF THE INVENTION

DETAILED DESCRIPTION OF THE INVENTION

Figure 1:
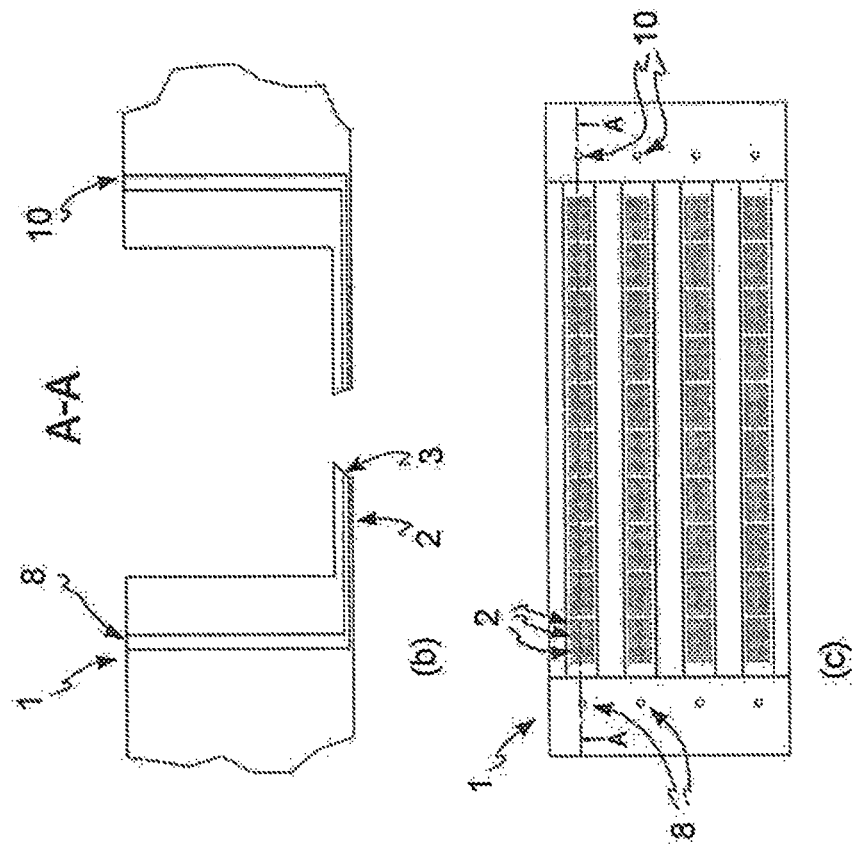
FIG. 1: exemplary diagram of an open reversed microwell system used in the method of the present invention, perspective view (a), vertical section (b) and top view (c).
Figure 1:
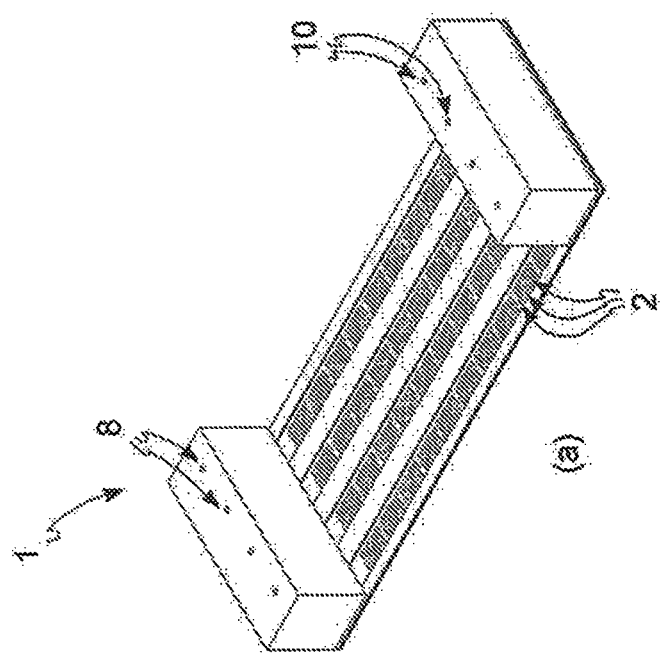

A microfluidic device (1), a kit comprising a tip (20) and an input region (18) of a microfluidic device (1), a discharge region (70) of said microfluidic device (1) are described herein. The present description also relates to a method for introducing and/or discharging one or more fluids from said microfluidic device (1) and a high-content analysis method in said microfluidic device (1).

Definitions

By interference coupling it meant herein a cooperation between two elements, so that said two elements can be considered as joined. When said two elements, in this case a tip and a vertical channel, are coupled by interference, a fluid charged into said tip and released in said vertical channel is forced to move within the channel, said interference coupling being such as to prevent the passage of fluid, i.e. said interference coupling is such as to mutually seal the two elements.

By connector it is meant herein any tubular, cylindrical, more or less tapered, converging or diverging element adapted to put two compartments in fluidic connection.

By semi-opening of the truncated cone it is meant the angle formed by the straight line generating said truncated cone with the straight line which forms the rotation axis thereof.

Fluids: any substance in liquid or gas form.

Biological sample: sample comprising cells obtained from a micro-organism, an animal and/or a human, preferably a human, where said sample is preferably selected from the group comprising biological fluids or biopsies. Said sample comprises suspended cells, or is a tissue. In a preferred embodiment, it is a sample of blood or a bone marrow aspirate. Alternatively, said biological sample consists of cultured cells, such as a cell line, or a composition comprising cultured cells and cells from a patient.

High-content assay: phenotypic assay conducted on cells.

Time-lapse: imaging technique involving a series of shots of the same field taken in a time sequence.

Ex-vivo: testing performed on a tissue obtained from an organism into an environment outside the organism itself, with minimal alteration of natural conditions.

Kit and Method for Introducing One or More Fluids in a Microfluidic Device

The present invention relates to a kit which comprises a tip (20), and to a microfluidic device (1) which comprises at least one microchannel (3) and an input region (8) which comprises at least one vertical channel (18), said tip (20) and said vertical channel (18) being dimensioned so to produce an interference coupling therebetween.

Said tip is selected from one of the tips commercially available which comprise at least one proximal portion intended to cooperate with a fluid dispensing system and an open tapered distal portion.

Figure 18:
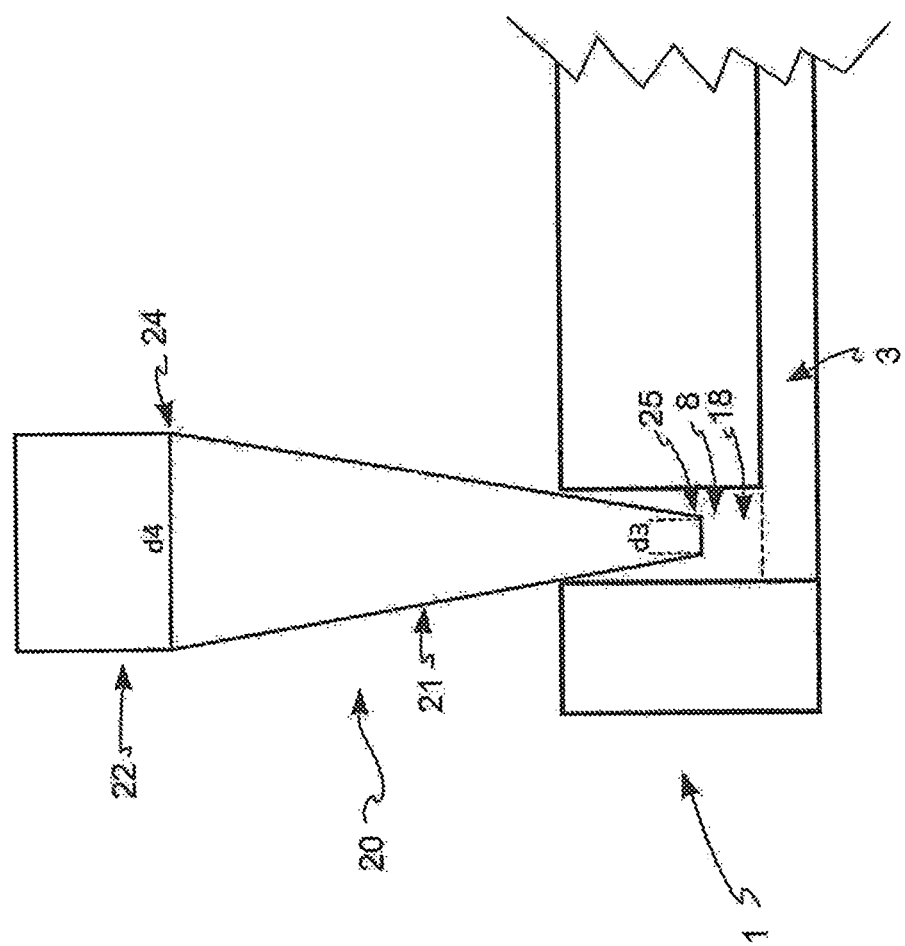
FIG. 18: diagram of the kit according to the present invention which includes a tip and a microfluidic device.

With reference to FIG. 18, said tip (20) comprises a proximal portion (22) intended to cooperate with a fluid dispensing system and a distal portion (21), said proximal portion of generally tubular configuration and said distal portion (21) open tapered where the terminal base (25) of said distal portion (21) has an outer diameter of dimensions d3, and the upper base (24) of the said distal portion (21) has an outer diameter of dimensions d4, where said input region (8) comprises a vertical channel (18) which leads, optionally through one or more connectors, into said at least one microchannel (3), the upwards opening of said vertical channel (18) having a diameter of d2, where d3<d2, said tip (20) and said vertical channel (18) being dimensioned so as to produce an interference coupling therebetween.

Figure 19:
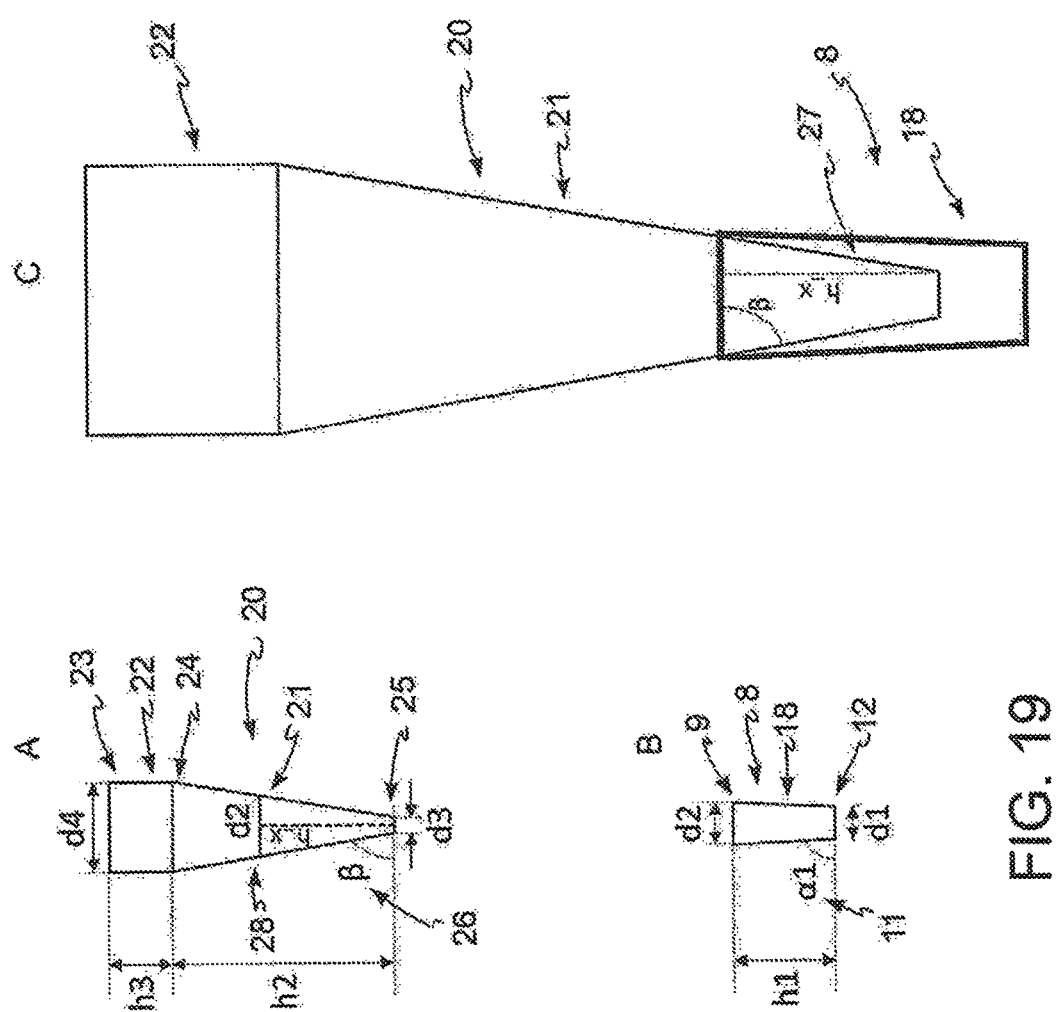
FIG. 19: schematic representation of an embodiment of the kit according to the present invention. (A) tip, (B) input region, (C) tip inserted in the input region.
Figure 20:
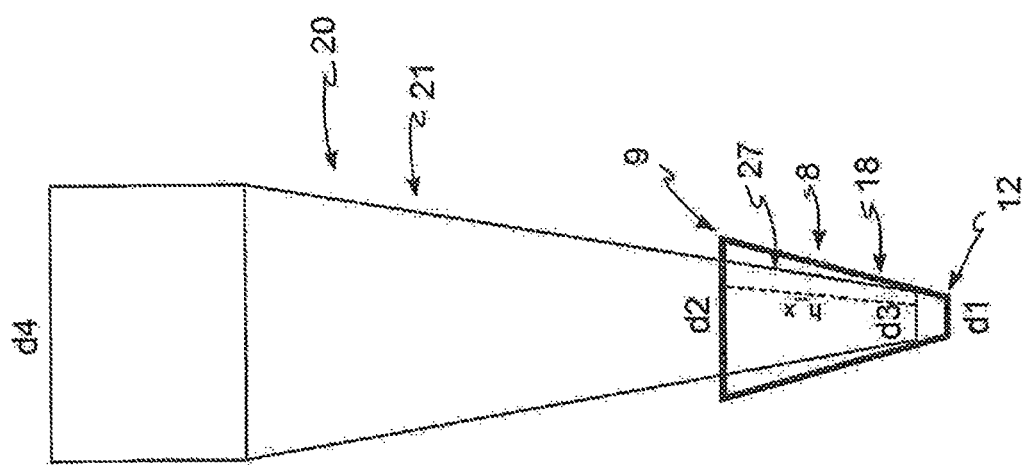
FIG. 20: schematic representation of an embodiment of the kit according to the present invention, tip inserted in the input region.

Said interference coupling typically occurs according to one of the modes shown in FIGS. 19 and 20. With reference to FIG. 19, said tip (20) and said channel (18) have as a sealed contact point the upper base (9) of said vertical channel (18). With reference to FIG. 20, the sealed contact point is within the vertical channel (18), in this version being the terminal base (25) of the distal portion (21) of the tip (20) to come into contact with the inner wall of said vertical channel (18). In both cases, sealed contact occurs. Preferably, said terminal portion (21) of said tip (20) and said vertical channel (18) are made of plastic and make the system resilient enough to ensure the seal, avoiding gaskets. In a particularly preferred embodiment, the system geometries described hereinafter ensure that the contact between said vertical channel (18) and said tip (20) does not occur in a single point but is distributed on a surface portion, further ensuring an effective seal. In particular, this condition is advantageously verified where the semi-opening angle of said terminal portion (21) of said tip and said vertical channel (18) are little different, preferably differ by less than 10°. Even more preferably, said vertical channel (18) a cylinder, optionally slightly tapered downwards.

With reference to FIG. 19A, the length of said distal portion (21) of said tip (20) is h2, the semi-opening of the truncated cone formed by said distal portion (21) is (90°-β) and the length of said proximal portion (22) is h3. Reference shall be made to the same FIG. 19A for a more exhaustive description or said tip, where the angle (26) measuring β and the longitudinal axis x which allows the definition of said semi-opening of the truncated cone are indicated.

FIGS. 20 to 24 and the following description are meant to describe some particularly preferred embodiments of the invention, and they do not limit the scope of protection thereof which extends to what claimed in claim 1.

In a preferred embodiment, the reference is to FIG. 19, in which said vertical channel (18) is a channel tapered downwards which has an upper base (9) and a lower base (12), said lower base (12) having a diameter of dimensions d1 and said upper base (9) having a diameter of dimensions d2, said vertical channel (18) having a height h1 and the semi-opening of the truncated cone formed by said tapered channel trunk is (90°-α1). In a preferred embodiment, α1 is 90° and said vertical channel (18) is a cylinder.

Preferably, said measures β and α1 differ from each other by up to 15°, preferably by 10°, even more preferably by a value of between 4 and 5°.

In a preferred embodiment, with reference to FIGS. 19A, 19C, said distal portion (21) of said tip (20) has a diameter section of dimensions d2 at a point (28) positioned along said distal portion (21) at a height h_x relative to the terminal base (25) of said distal portion, said height h_x being smaller than the distance between said upper base (9) of said vertical channel (18) and the input point in said microchannel (3), wherein said distance is h1 in the absence of any connector, where d3<d2<d4 and (90°-α1)<(90°-β), preferably α1 is of between 80° and 90°, even more preferably is equal to 90°. In particular, said tip (20) fits into said input region (8) which is said vertical channel (18) by a portion (27) having length h_x, i.e. said tip fits into said input region (8) reaching the interference coupling point before reaching the microchannel (3), i.e. said tip and said vertical channel (18) comprised in said input region (8) reach the sealing position when the portion of said tip inserted in said vertical channel (18) is not such as to make said tip reach said microchannel (3). In this embodiment, (90°-α1)<(90°-β) and h_x=((d2-d3)/2)*tgβ, preferably α1 is of between 80° and 90°, even more preferably is 90°.

Figure 22:
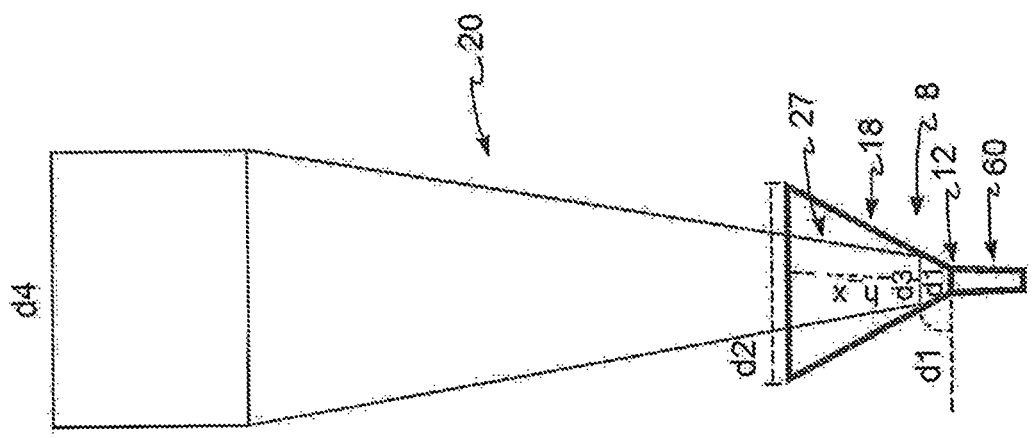
FIG. 22: schematic representation of a further embodiment of the kit according to the present invention, tip inserted in the input region comprising a vertical channel and a connector.

Alternatively, with reference to FIG. 22, said tip (20) fits into said vertical channel (18) comprised in said input region (8) by a portion (27) having length h_x, where d1<d3<d2, (90°-α1)>(90°-β). Again with reference to the same FIG. 22, optionally said input region (8) comprises a connector (60), having an upper base (12) which coincides with the lower base (12) of said vertical channel (18).

Figure 21:
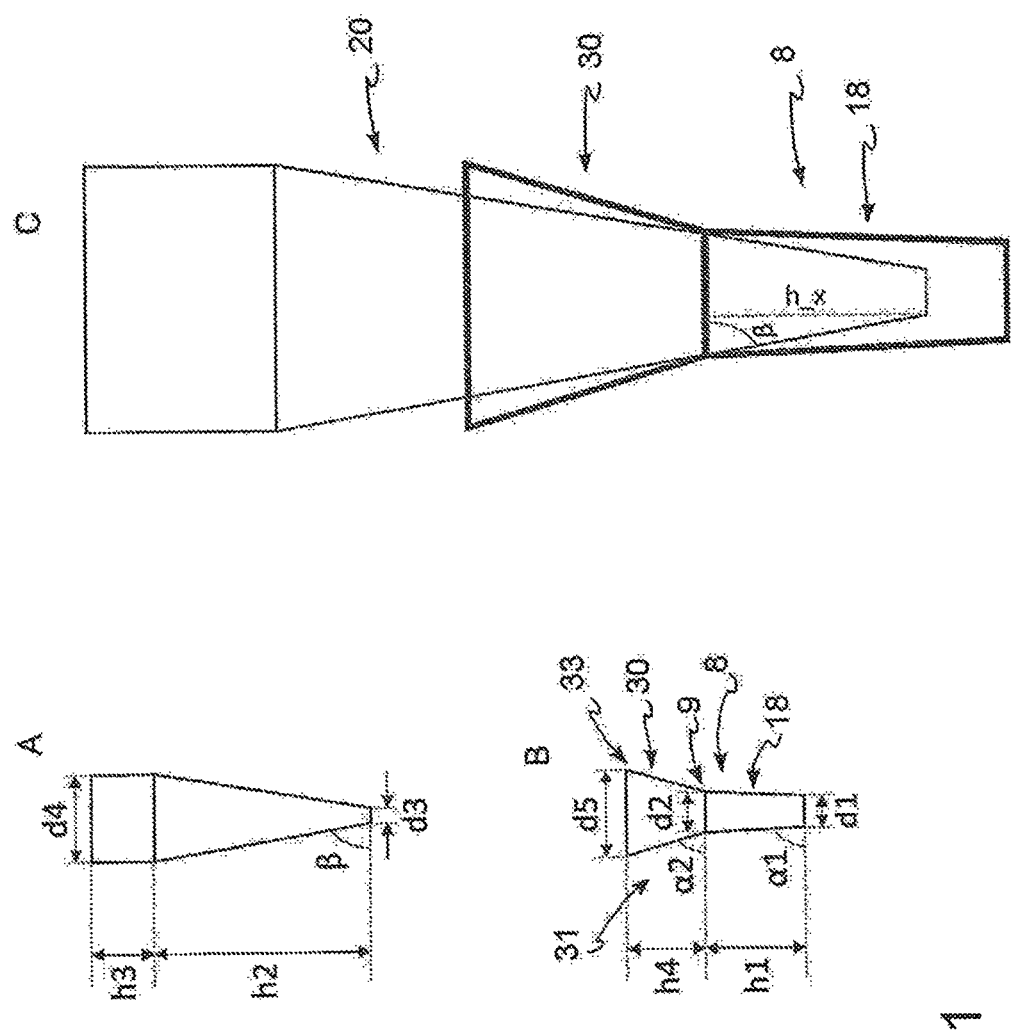
FIG. 21: schematic representation of a further embodiment of the kit according to the present invention. (A) tip, (B) input region, (C) tip inserted in the input region.

In an alternative embodiment, with reference to FIG. 21, said input region (8) further comprises a flare portion (30) hollow truncated conical in shape, having a height h4 and an upper base (33) and a lower base (9) which coincides with the upper base (9) of said vertical channel (18), said upper base (33) having a diameter d5 greater than diameter d2 of said lower base (9), where the half-opening of the truncated cone forming said flare portion (30) is (90°-α2) where (90°-α2)>(90°-β).

Figure 23:
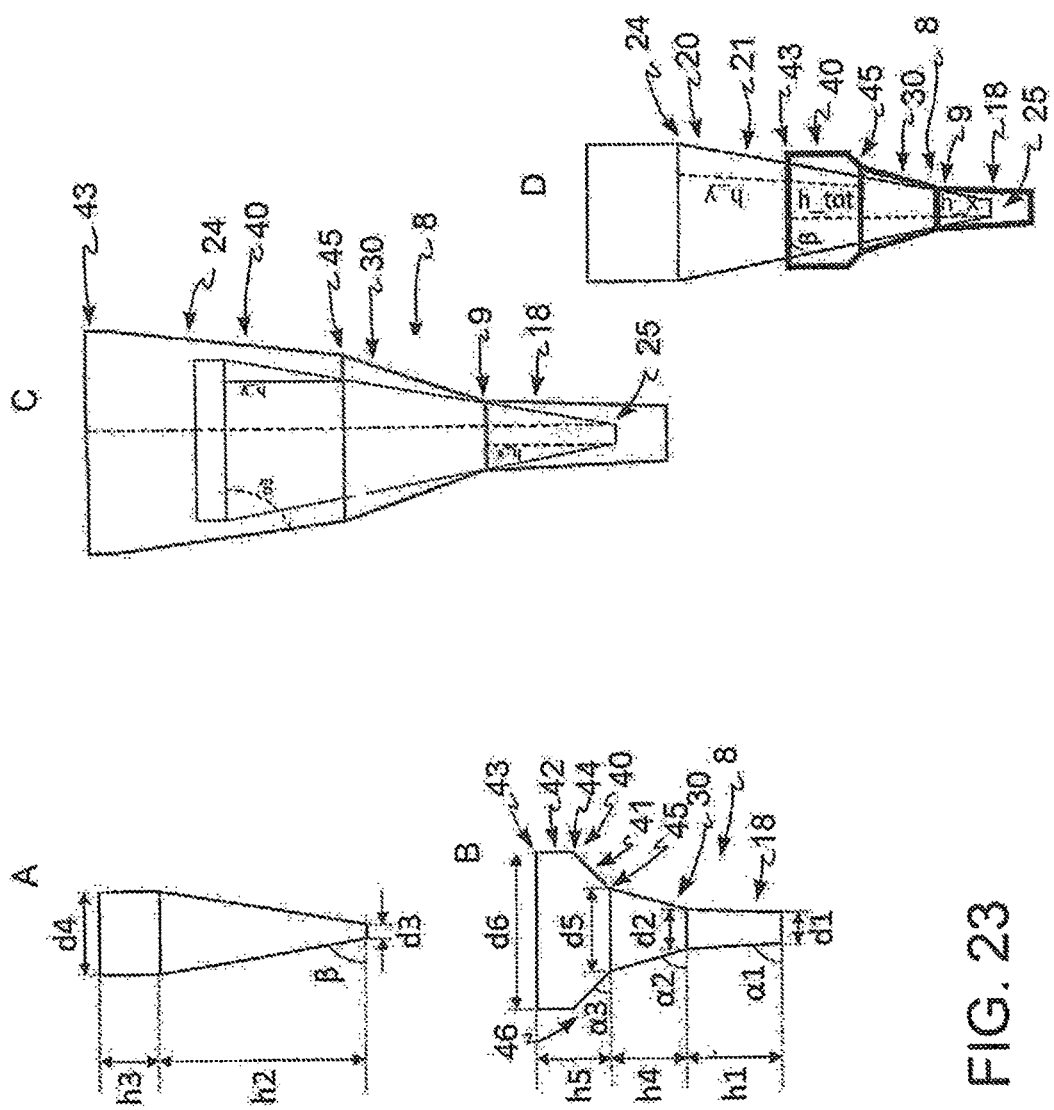
FIG. 23: schematic representation of a further embodiment of the kit according to the present invention. (A) tip, (B) input region, (C) tip inserted in the input region, (D) tip inserted in the input region in an alternative embodiment.

Preferably, with reference to FIG. 23, said input region (8) further comprises, above said flare portion (30), a storage region (40) which comprises at least two portions: an upper portion (42) and a lower portion (41), wherein said upper portion (42) has a generally tubular shape having an upper base (43) and a lower base (44) of diameter d6 and said lower portion (41) is tapered downwards and has an upper base (44) which coincides with said lower base (44) of said upper portion (42) and a lower base (45) of diameter d5, said storage region (40) has a height h5 and the half-opening of the truncated cone which forms said lower portion (41) is (90°-α3), where α3 is smaller than or equal 90°, preferably α3 is 0°.

Where said input region also comprises said storage region (40), said tip (20) fits into said input region (8) by a length greater than the length of said distal portion (21) of said tip (20), the distance between said terminal base (25) of said distal portion (21) of said tip (20) and the upper base (43) of said storage region (40) is h_tot, (h_tot being>h2) and the distance between said upper base (24) of said distal portion (21) of said tap (20) and the lower base (45) of said storage region (40) is h_y, 2*h_y*cotα3+d5 being>d4.

Alternatively, and with reference to FIG. 23D, said tip (20) fits into said input region (8) by a length smaller than the length of said distal portion (21) of said tip (20), the distance between said terminal base (25) of said distal portion (21) of said tip (20) and the upper base (43) of said storage region (40) is h_tot and the distance between said end base (25) of said distal portion (21) of said tip (20) and the upper base (9) of said vertical channel (18) is h_x, h_tot being=h_x+h4+h5 and the distance between said upper base (24) of said distal portion (21) of said tip (20) and the lower base (45) of said storage region (40) is h_y, h_y being=h2-h_x-h4.

Figure 24:
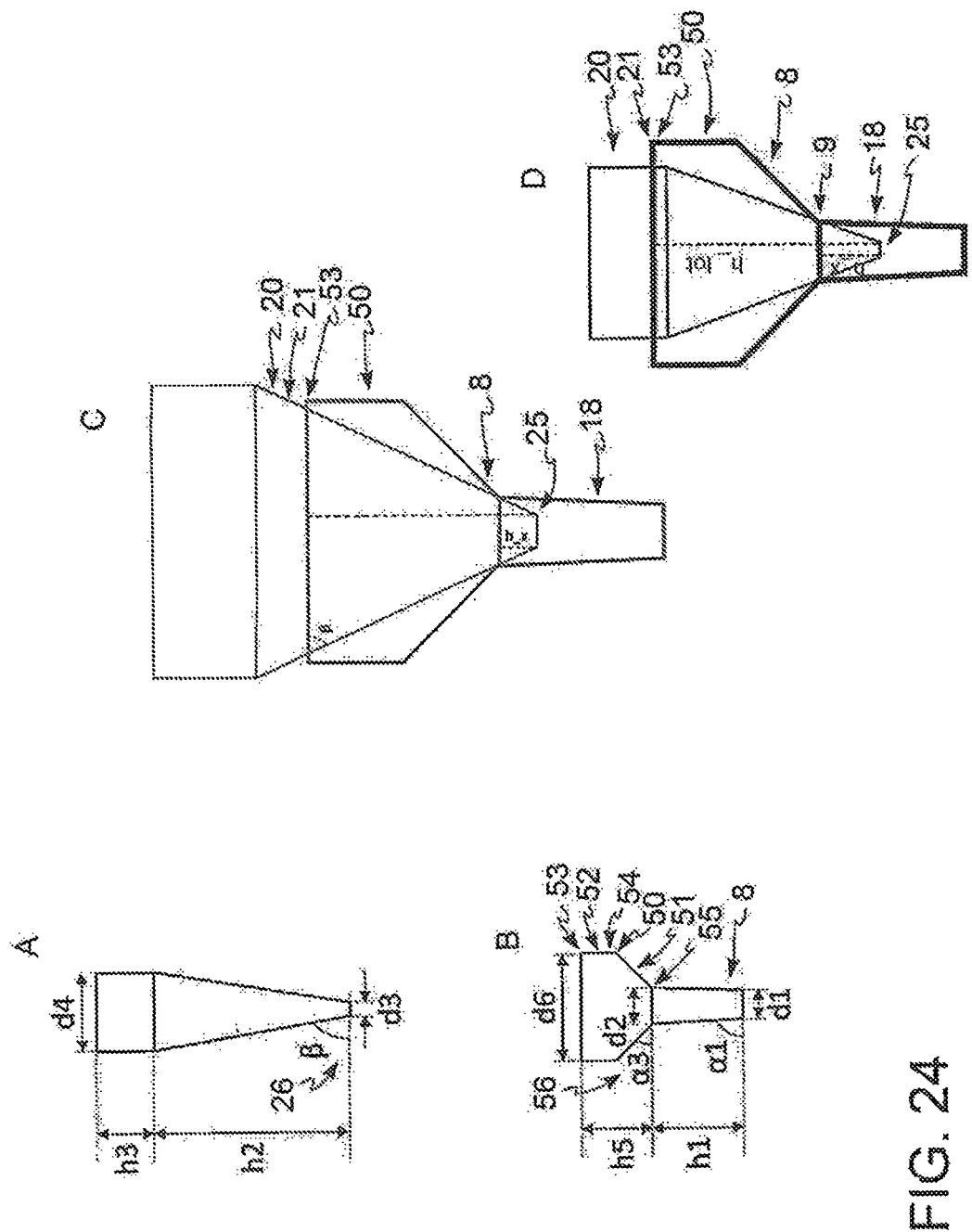
FIG. 24: schematic representation of a further embodiment of the kit according to the present invention. (A) tip, (B) input region, (C) tip inserted in the input region, (D) tip inserted in the input region in an alternative embodiment.

In a further embodiment, with reference to FIG. 24, said input region (8) further comprises a storage portion (50) which comprises at least two portions: an upper portion (52) and a lower portion (51), wherein said upper portion (52) has a generally tubular shape having an upper base (53) and a lower base (54) of diameter d6 and said lower portion (51) is tapered downwards and has an upper base (54) which coincides with said lower base (54) of said upper portion (52) and a lower base (55) of diameter d2, said storage region (50) has a height h5 and the half-opening of the truncated cone which forms said storage portion (50) as (90°-α3), where (90°-α3)>(90°-β).

Where said input region comprises said storage region (50), said tip (20) fits into said input region (8) by a length smaller than the total length of said tip (20), the distance between said terminal base (25) of said distal portion (21) of said tip (20) and the upper base (53) of said storage region (50) is h_tot, h_tot being smaller than or equal to h2 and (2*h_tot*cotβ+d3)<d6.

Alternatively, with reference to FIG. 24D, said tip (20) fits into said input region (8) by a length smaller than the total length of said tip (20), the distance between said terminal base (25) of said distal portion (21) of said tip (20) and the upper base (53) of said storage region (50) is h_tot, and the distance between said end base (25) of said distal portion (21) of said tip (20) and the upper base (9) of said vertical channel (18) is h_x, where h_tot>h2 and h_tot=h_x+h5.

Those skilled in the art understand that further embodiments are possible.

The embodiment which involves the presence of a storage tank in said input region (8) is advantageously used whenever the evaporation in the microfluidic device is to be controlled. In fact, said storage region can be advantageously left filled with the fluid charged in the microfluidic device so that, also when long incubation times are needed, there are no undesired evaporation effects.

The optional presence of the storage region allows to have a vertical channel (18) and, optionally, connectors (60) whose volumes are reduced to a minimum, so as to avoid wastage of fluids, having one or more storage tanks for use only when needed.

The possibility of having a flare portion (30) offers the advantage of providing an opening wide enough to allow a tip (20) fitting in said input region (8) also in a non-centered manner along the vertical central axis of the input channel (18) to enter into said flare portion P) and then during the downward movement of said tip (20) in the input channel (18), by sliding the same tip along the inner walls of the flare portion and the input channel, even with a possible bending/curving of the tip (20).

Optionally, said microfluidic device (1) also comprises an impedance meter calibration plate and said tip (20) is connected to a dispensing system provided with an impedance detection system.

Optionally, said microfluidic device comprises a closing element of said input region (8), for example said closing element is a cap or a protective film. This protective film is, in one embodiment, of elastomer material, for example silicone.

The surprising solution highlighted by the authors of the present invention and described in claim 1 allows, with the method described hereinafter, to manage the introduction of one or more fluids in a microfluidic device only by using the interference coupling which takes place between said tip and said vertical channel, without the use of pumps or valves.

In particular, the method of loading/unloading fluids in the microfluidic device (1) comprised in the kit described and claimed consists of the following steps:

a) Providing a kit according to one of claims 1 to 8;
b) Optionally, charging a fluid into said tip (20);
c) Positioning said tip (20) above said input region (8) and inserting it up to reaching an interference coupling position between said distal region (21) of said tip (20) and said vertical channel (18) in said input region (8);
d) Releasing the fluid contained in said tip (20) in said microfluidic device (1) through said input region (8) or, alternatively, with the same tip (20) suctioning fluid already contained in said microfluidic device.

When the method is applied to the suctioning of fluid and not to the release, and said fluid is a liquid, conveniently said vertical channel (18) and said optional connectors (60) also contain said liquid, or said liquid is not only contained in the microfluidic device. The presence of liquid in contact with the tip (20), by lowering the surface tension, facilitates the intake process which would be more difficult if said tip suctioned air before suctioning the fluid contained in said microfluidic device.

Microfluidic Device

A microfluidic device is also described, which is a reversed open microwell system which comprises an array of open microwells 2, at least one microchannel 3, at least one input port 8 for reagents and/or for one or more biological samples and at least one output port 10 for them, said input and output ports being in microfluidic communication with one or more of said microchannels 3, wherein said microchannel 3 has a cross-section area of micrometric dimensions and provides fluid to said microwells 2, wherein said reversed open microwell system is, in one embodiment, inserted in an automated management system which comprises the following features: an incubator at controlled temperature, humidity and $CO_2$, fluid dispensing system, phase-contrast and fluorescence image acquisition.

Said automated management system is achieved by assembling elements which are known in the art as a temperature, humidity and $CO_2$ control incubator, microplate pipetting systems, fluorescence and phase-contrast microscopy lenses connected to an image acquisition camera, such as a CMOS or CCD camera, where said elements are managed in whole or in part by software known to those skilled in the art through hardware connected thereto.

In a particularly preferred embodiment, each microchannel 3 is associated with an input port 8 and an output port 10.

In a preferred embodiment, the microfluidic device (1) also comprises reservoirs 6, 7, where said reservoirs are at least one reservoir 6 for reagents and at least one reservoir 7 for one or more biological samples. Said reservoirs are selected from the group comprising: plates, one or more multiwell plates, such as 96-well plate, eppendorf tubes. Said reservoirs 6 and 7 may be 2, or 4, 8, 16, 24, 48, 96, 384.

Figure 3:
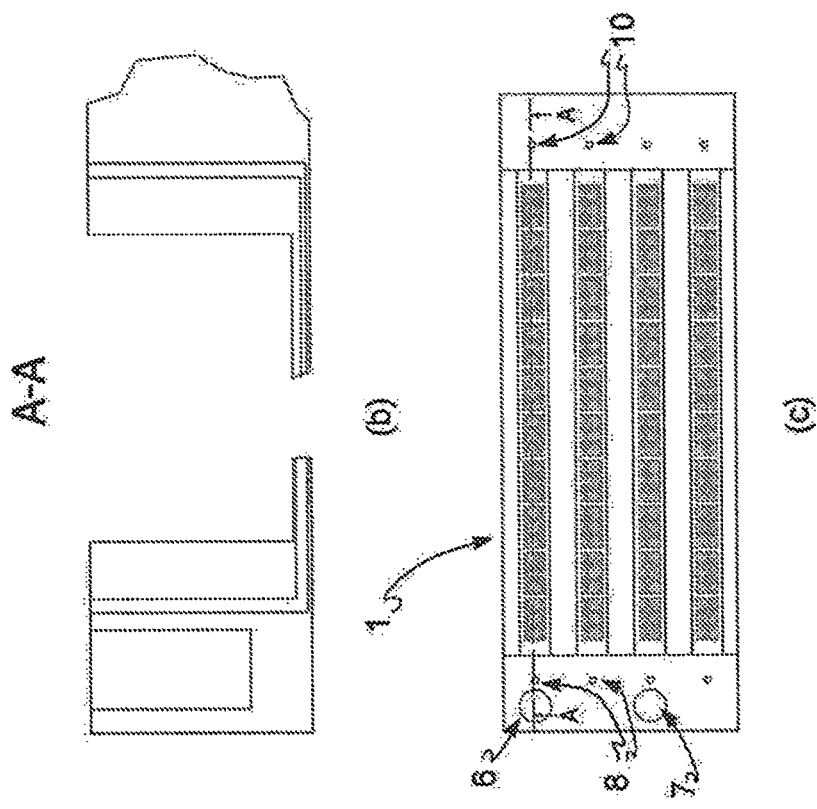
FIG. 3: diagram of an open reversed microwell system used in a preferred embodiment of the method of the present invention, perspective view (a), vertical section (b) and top view (c).
Figure 3:
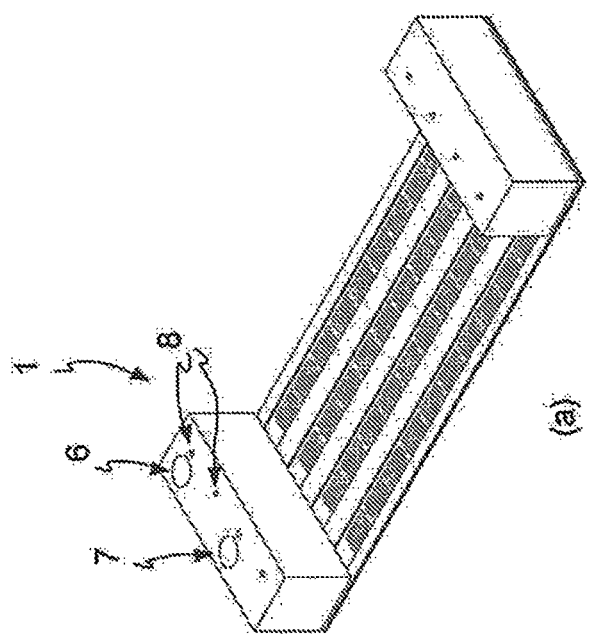

In a preferred embodiment, outlined in FIG. 3, 26, said reservoirs 6, are integrated in said open reversed microwell system 1.

Figure 4:
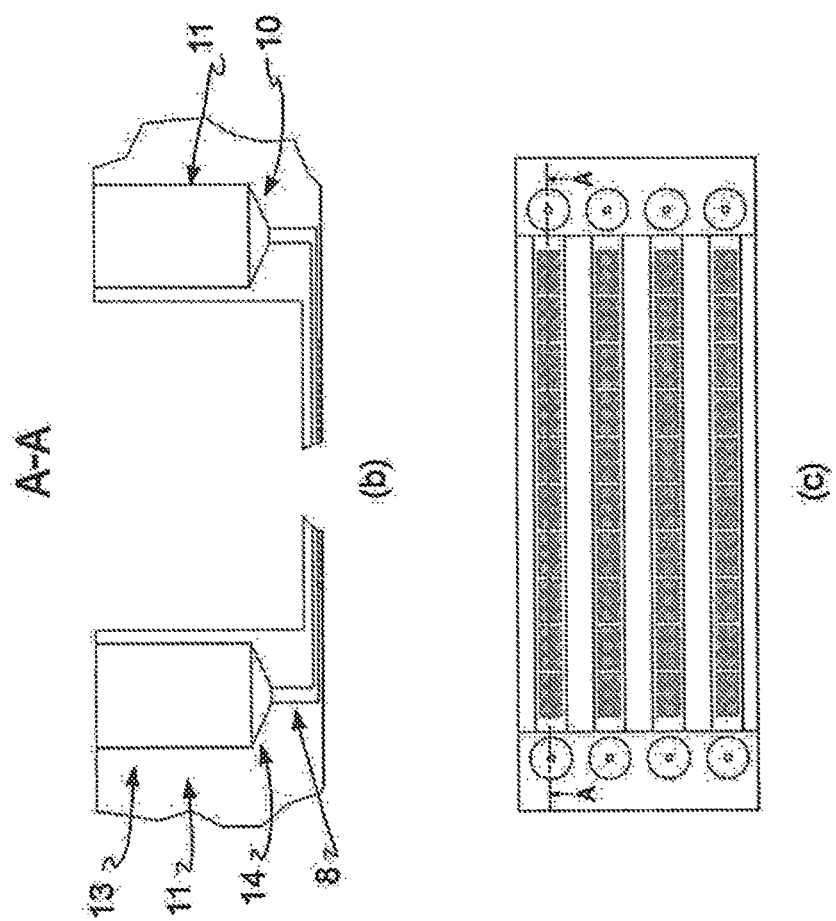
FIG. 4: diagram of an open reversed microwell system used in a further preferred embodiment of the method of the present invention, perspective view (a), vertical section (b) and top view (c).
Figure 4:
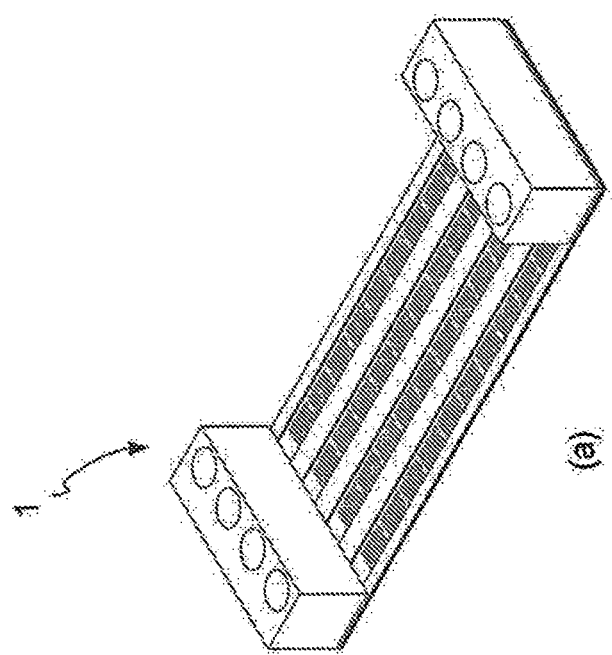

In a further embodiment, outlined in FIG. 4, said at least one input port 8 for reagents also comprises a storage area 11. In this embodiment, said reagents and/or said biological sample are parked in said storage area before crossing said input port 8. Also said output port 10 may optionally comprise a storage area 11. Said storage area is preferably located above said input port and in a preferred embodiment, advantageously consists of two portions: an upper portion 13 and a lower portion 14. Said upper portion 13 has a cylindrical shape and said lower portion 14 has a funnel shape, where said upper portion 13 is a cylinder with a base having a diameter greater than the diameter of said input port 8 and said lower portion 14 is a funnel which connects said upper portion with said input port.

Discharge Region

Figure 27:
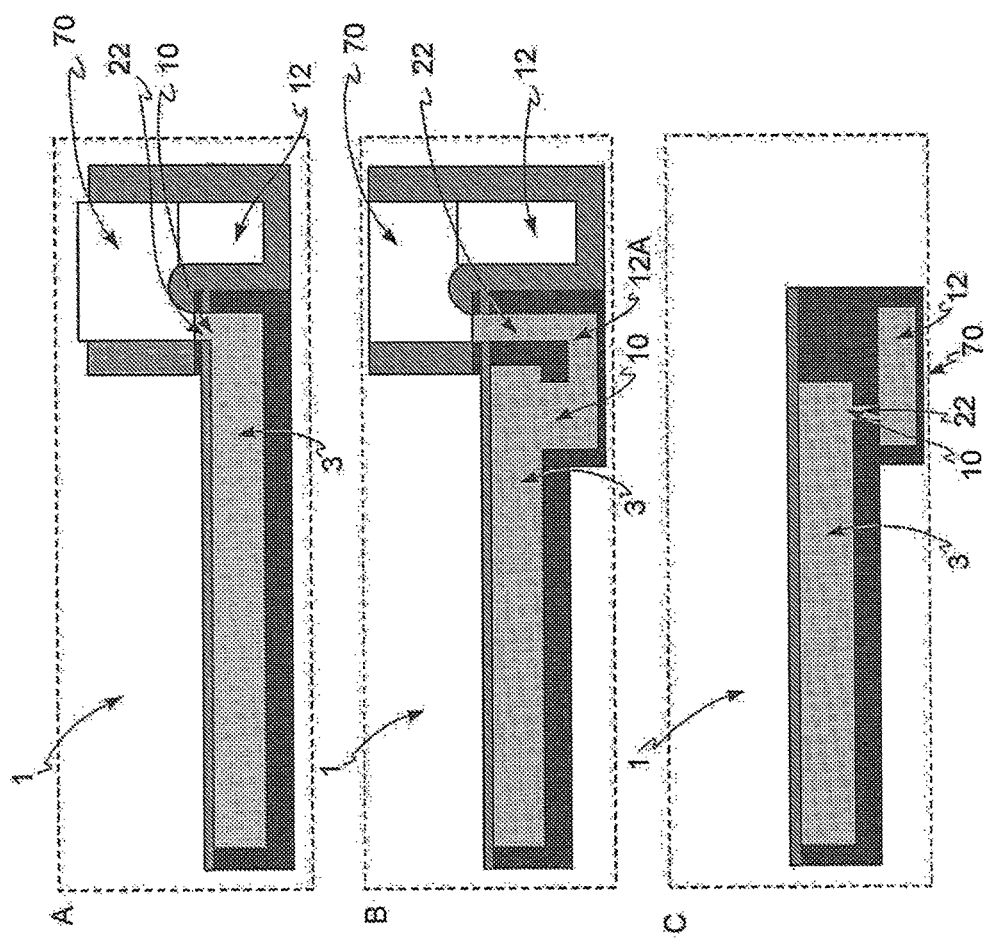
FIG. 27: three embodiments, in panels A, B and C, of the discharge region (70) of a microfluidic device (1).
Figure 28:
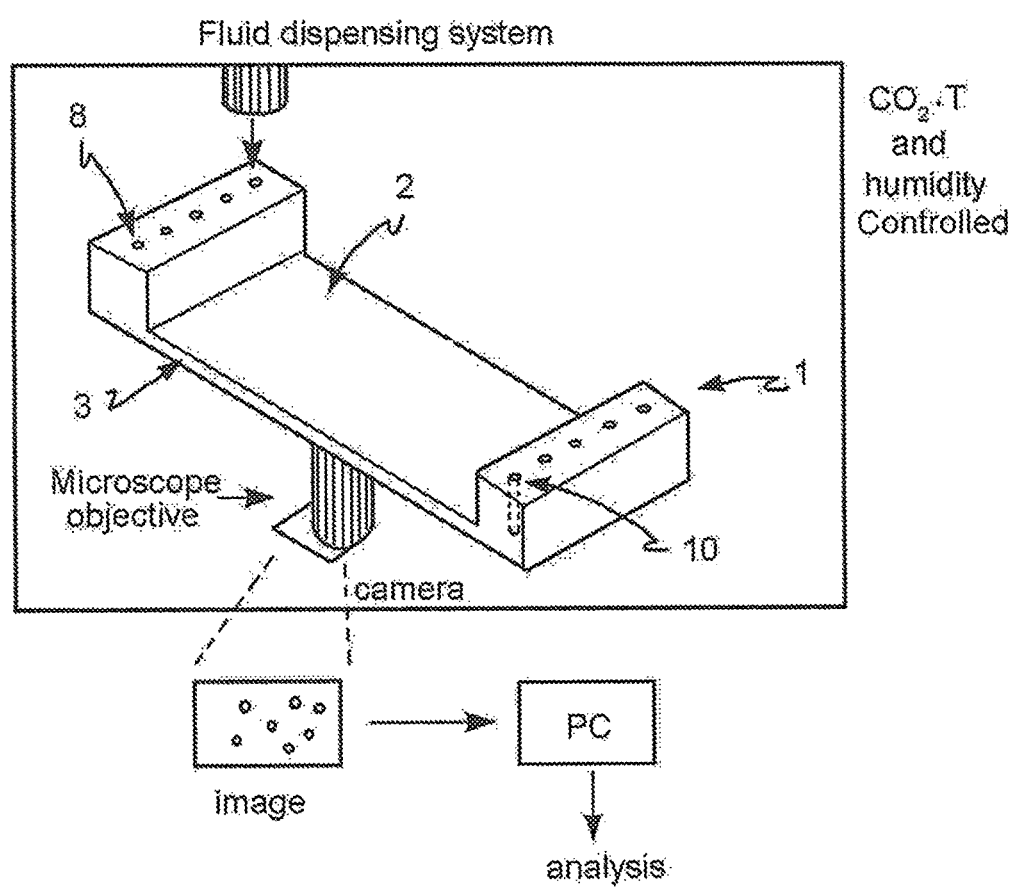
FIG. 28: schematic representation of the automated management system in which the microfluidic device is inserted (1).

In a further embodiment, with reference to FIG. 27, said discharge region (70) intended to discharge the fluids from said microfluidic device (1) which comprises at least one input region (8), comprises a discharge container (12) in fluidic connection with said microfluidic device (1) through at least one discharge channel (22) and an output port (10). In one embodiment, said fluid, pushed by a pressure applied in said input region (8) in said microfluidic device (1), unidirectionally reaches said discharge container (12) where volume V of said fluid is smaller than or equal to the volume of said discharge container (12). Preferably, with reference to FIG. 27A, said discharge channel (22) emerges from the at least one microchannel (3) comprised in said microfluidic device (1) and is a siphon.

Preferably, the diameter of said discharge channel (22) is such that the siphon exerts a capillary force on the fluid contained in said microchannel (3).

In a further embodiment, outlined in FIG. 27C, said discharge channel (22) is located on the bottom of at least one microchannel (3) and is almost orthogonal thereto and puts said at least one microchannel (3) in communication with said discharge container (12) which is placed below the same microchannel (3).

In a further embodiment, with reference to FIG. 27B, said output port (10) is placed on the bottom of said at least one microchannel (3) and leads into a first discharge container (12a), positioned below said microchannel (3) and said discharge channel (22) leading to said discharge container (12) protrudes from said first discharge container (12a). Preferably, with reference to FIG. 27B, the discharge channel (22) is a siphon.

Said discharge channel (22) preferably has a cross-sectional area of micrometric dimensions, said dimensions being between 100 μm and 5 mm, preferably between 500 μm and 2 mm.

In a particularly preferred embodiment, the kit according to the present invention comprises a microfluidic device as described above.

Even more preferably, the kit according to the present invention comprises the microfluidic device as described above, also characterized by the fluid discharge region described above.

Figure 25:
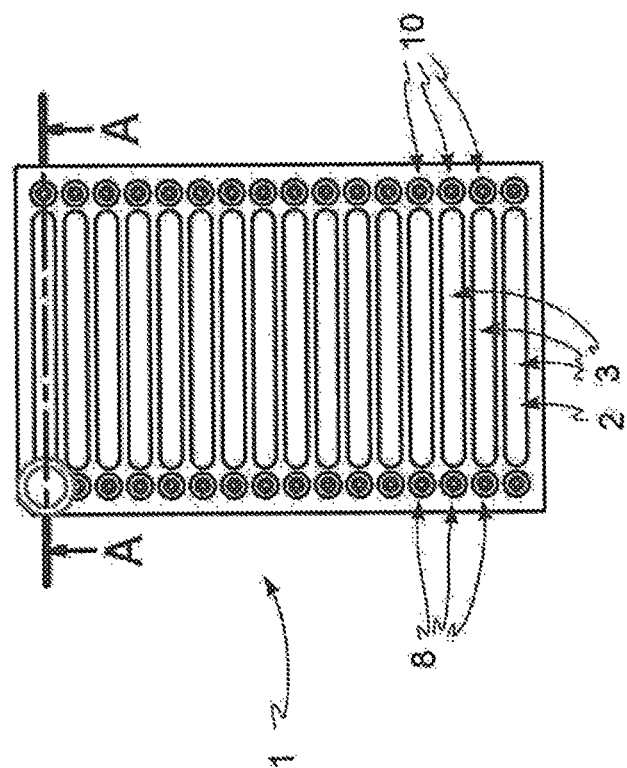
FIG. 25: open reversed microwell system according to the present invention, top view.

In a preferred embodiment, depicted in FIG. 25, the microfluidic device (1) comprises an input region (8) adapted to be included in the kit according to one of claims 1 to 8 and a discharge region (70) according to claim 10.

Therefore, the present invention relates to a method for charging/discharging fluids from a microfluidic device, where said method comprises:

a) Providing a microfluidic device (1) comprising an input region (8) and a discharge region (70) according to one of claims 1 to 6, wherein said microfluidic device (1) is charged with at least a first fluid;

b) Optionally, exerting a pressure on said at least a first fluid entering said microfluidic device (1);

c) Alternatively, arranging a discharge region (70) where said discharge channel (22) has a diameter such as to make said fluid pass from said microfluidic device to said discharge channel by capillarity;

characterized in that, where volume V of said at least a first fluid is smaller than or equal to the volume of said discharge container (12), said at least one fluid unidirectionally reaches said discharge container (12).

In a further embodiment, said method further comprises:
introducing a second or further fluid through said input region (8) in said microfluidic device (1), where said first, second and/or further fluids are independently equal or different from one another and are selected from the group comprising liquids and gases;

optionally, said second and/or further fluid completely replaces in said microchannel (3) or in said microchannel (3) and in said reversed open microwells (2), when present in said microfluidic device (1), the fluid introduced before;

characterized in that said first, second and/or further fluids do not mix with one another.

Figure 26:
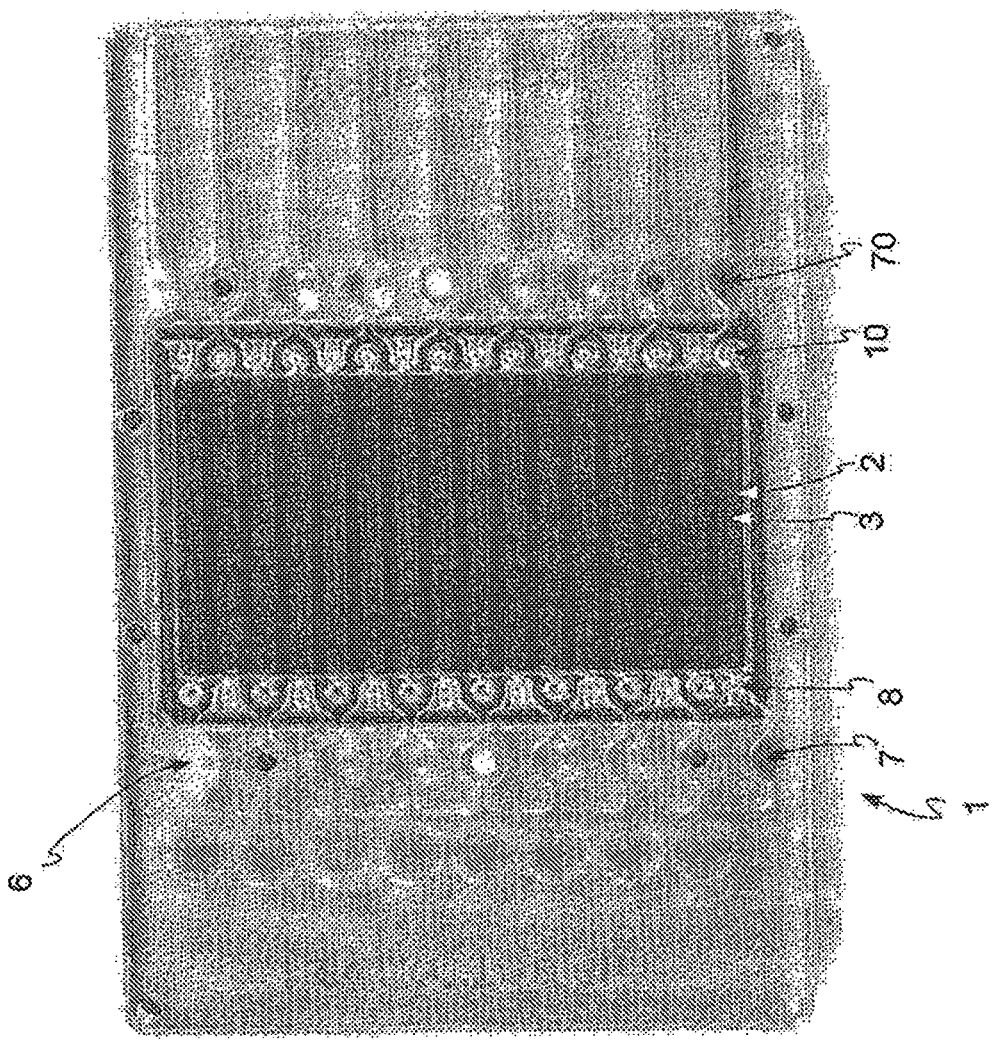
FIG. 26: open reversed microwell system according to a further embodiment, top view.

In a further embodiment, depicted in FIG. 26, the microfluidic device (1) is an open reversed microwell microfluidic device (2) and further comprises reservoirs (6) for reagents and reservoirs (7) for one or more biological samples.

In a particularly advantageous embodiment, said device comprises 16 microchannels (3), each having an input region (8) and an output region (10), wherein each of said microchannels (3) faces towards 1200 open reversed microwells.

In addition to the advantages outlined above, it should be noted that the microfluidic device (1) which comprises the input region (8) according to the present invention is particularly advantageous, since it:

allows the direct interfacing, i.e. without the aid of seals, of a microfluidic device with systems commonly used in the field for the management and transfer of liquids and gases;

allows to take fluids from plates or containers by inserting them under pressure into microchannels of the microfluidic device, where the volumes involved in such plates or containers are greater or much greater (e.g. 50 µl or more, 300 µl or more) than those typical of the microchannel (40 µl or less) and where the transfer is done using standard tools already commonly used in combination with the above plates or containers, allows to insert fluid sequences in the microfluidic device even of different types, without the use of additional equipment, such as pumps or valves.

Fluid Charging/Discharging Method from a Microfluidic Device

A further aspect of the present invention is a method for managing a microfluidic device (1) with open reversed microwells (2) comprising at least one input region (8), at least one output region (10) and at least one microchannel (3), wherein said method comprises:

introducing at least a first fluid through said input region (89 in said microfluidic device (1);

optionally introducing a second or further fluid through said input region (8) in said microfluidic device (1), where said first, second and further fluids are independently equal or different from one another and are selected from the group comprising liquids and gases;

optionally, said second or further fluid completely replaces in said microchannel (3) or in said microchannel (3) and in said reversed open microwells (2), the fluid introduced before;

optionally suctioning from said input region (8) the volume of fluid contained in the microchannel (3), leaving said fluid in said microwells (2).

In one embodiment, said method is implemented in a microfluidic device (1) comprising an input region (8) according to one of claims 1 to 8 and a discharge region (70) according to claim 10 and is characterized in that if the overall volume of said first and optionally, second and further fluid introduced in said microfluidic device (1) is smaller than the volume of said discharge container (12), said fluids do not mix with one another.

Method for the High-Content Analysis of Biological Samples

The method described hereinafter surprisingly allows not only an analysis in time-lapse but also processing during said time-lapse analysis. That is, with the method of the present invention it is possible not only to monitor the same sample at different times (typical time-lapse analysis), but also handle the same sample at different times, the surrounding conditions varying over time and in a controlled and automated manner. As an example, the methodology described herein allows to evaluate, for each individual cell, the variation of morphological and functional parameters following a controlled exposure to a pharmacological agent, where said agent is added during such monitoring. Alternately, with the same technique, a dynamic analysis of the sample is possible, where dynamic analysis means herein a sample analysis performed at different times after the exposure to treatments of interest. Moreover, with the dynamic analysis carried out according to the present invention, it is possible to identify a cell sample insensitive to a treatment so as to expose it to a different treatment. The method claimed herein allows the implementation of a large scale high-content assay with processing in time-lapse, operator-independent, having equipment which can be installed in any analysis laboratory.

The method of the present invention is implemented in an open reversed microwell system whose structure is exemplified in FIG. 1. Said open reversed microwell system 1 comprises a series of microsells 2, open at both ends, arranged as a matrix, Said open reversed microwell system 1 further comprises at least one microchannel 3, wherein said at least one microchannel 3 has a cross-sectional area of micrometric size and provides fluid to said microwells 2. Said system further comprises at least one input port 8 for reagents and/or one or more biological samples and at least one output port 10 thereof, said input and output ports being in microfluidic communication with one or more of said microchannels 3.

In a particularly preferred embodiment, each microchannel 3 is associated with an input port 8 and an output port 10.

In a preferred embodiment, said reagents are contained in reservoirs 6, 7 where said reservoirs are at least one reservoir 6 for reagents and at least one reservoir 7 for one or more biological samples. Said reservoirs are selected from the group comprising: plates, one or more multiwell plates, such as 96-well plate, eppendorf tubes. Said reservoirs 6 and 7 may be 2, or 4, 8, 16, 24, 48, 96, 384.

Figure 2:
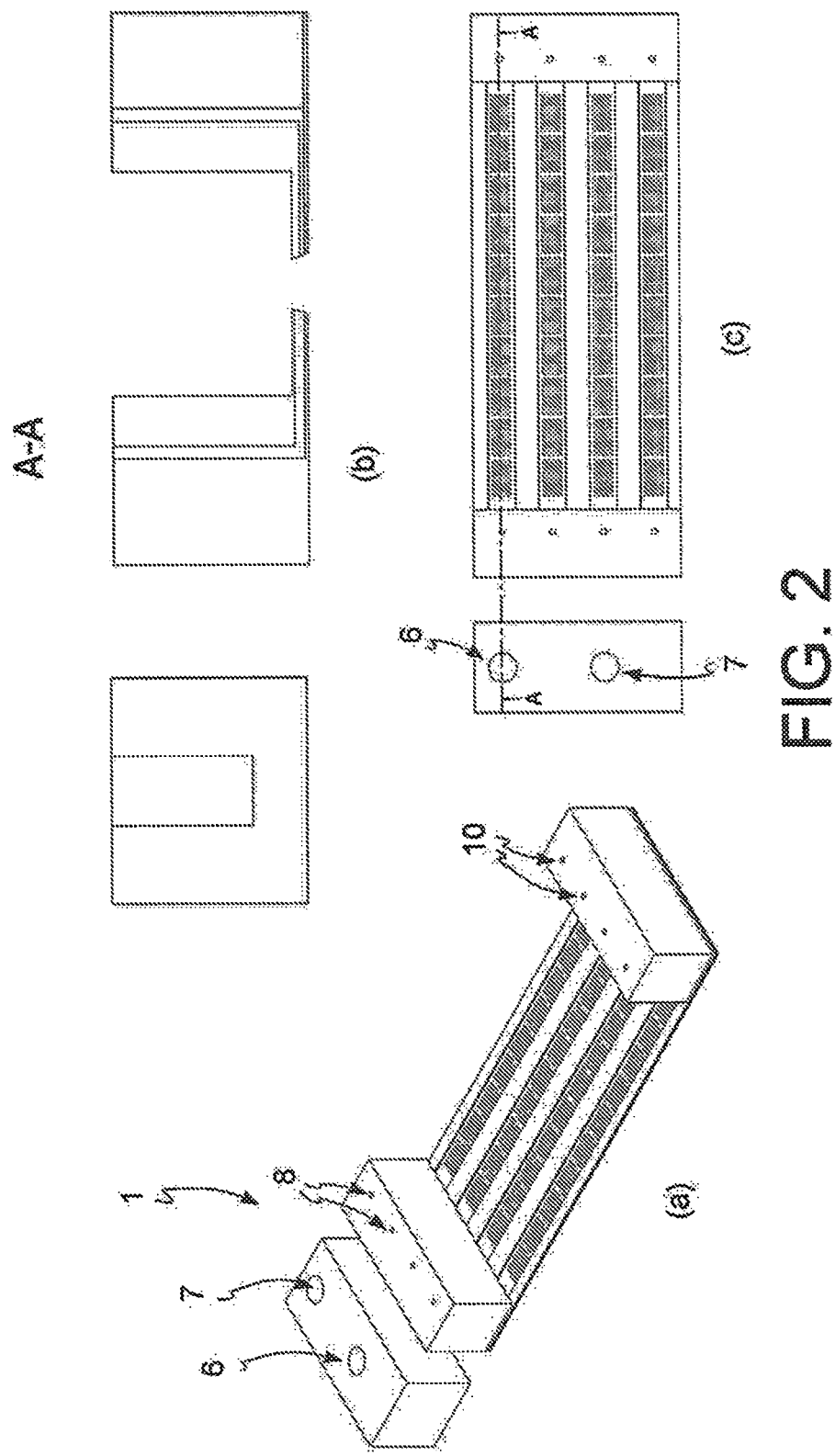
FIG. 2: diagram of an open reversed microwell system used in a further embodiment of the method of the present invention, perspective view (a), vertical section (b) and top view (c).

In one embodiment, outlined in FIG. 2, said reservoirs 6, 7 are external to said open reversed microwell system 1. In a preferred embodiment, outlined in FIG. 3, said reservoirs 6, 7 are integrated in said open reversed microwell system 1.

In a further embodiment, outlined in FIG. 4, said at least one input port 8 for reagents also comprises a storage area 11. In this embodiment, said reagents and/or said biological sample are parked in said storage area before crossing said input port 8. Also said output port 10 may optionally comprise a storage area 11. Said storage area is preferably located above said input port and in a preferred embodiment, advantageously consists of two portions: an upper portion 13 and a lower portion 14. Said upper portion 13 has a cylindrical shape and said lower portion 14 has a funnel shape, where said upper portion 13 is a cylinder with a base having a diameter greater than the diameter of said input port 8 and said lower portion 14 is a funnel which connects said upper portion with said input port.

The present invention also relates to a method for the large-scale, high-content analysis of biological samples, wherein said biological samples are as defined as above, which comprises the following steps, not necessarily in this order:

a) Providing a reversed open microwell system which includes an array of open microwells 2, at least one microchannel 3, at least one input port 8 for reagents and/or one or more biological samples and at least one output port 10 for them, said input and output ports being in microfluidic communication with one or more of said microchannels 3, wherein said microchannel 3 has cross-section area of micrometric dimensions and provides fluid to said microwells 2;

b) Providing an automated management system of said reversed open microwell system which comprises the following features: incubator at controlled temperature, humidity and $CO_2$, fluid dispensing system, phase-contrast and fluorescence image acquisition;

c) Placing said reversed open microwell system 1 in said automated system;

d) Charging reagents through one or more of said input ports 8 for reagents, where said reagents comprise: filling buffer and/or washing solution and/or one or more drugs and/or one or more dyes, and/or one or more labeled antibodies and or one or more cell viability markers;

e) Charging said one or more biological samples through one or more of said input ports 8;

i) Optionally, dyeing said cells with one or more dyes and/or one or more labeled antibodies and or one or more cell viability markers;

j) Acquiring images from one or more of said microwells 2, wherein said images are defined images T0;

p) Classifying the cells displayed, wherein said classification is made with morphological and/or functional parameters detected from the images T0.

In one embodiment, said open reversed microwell system is the microfluidic device according to claim 9; in a further embodiment, it is the microfluidic device according to claim 11, or is a microfluidic device 19 which also comprises the kit according to one of claims 1 to 8.

In one embodiment, where said reagents and biological sample are contained in 6, 7, said reservoirs 6, 7 are external to said open reversed microwell system 1, as outlined in FIG. 2, and said charging of reagents and of the at least one biological sample is done manually, i.e. by means of automated fluid dispensing systems, taking from the reservoirs and charging into the input ports 8. Preferably, said reservoirs 6, 7 are inserted in the automated system with the open reversed microwell system.

In an even more preferred embodiment, outlined in FIG. 3, said reservoirs 6, 7 are integrated into said open reversed microwell system 1 and said charging of reagents and of the at least one biological sample is done manually, i.e. by means of automated fluid dispensing systems, taking from the reservoirs and charging into the input ports 8. Alternatively, said reservoirs 6, 7, integrated in said open reversed microwell system 1, are in fluidic communication with said at least one input port 8.

Also when said input port 8 comprises said storage area 11, said reservoirs 6, 7 are arranged as described above, i.e. are external or integrated into the open reversed microwell system.

In a preferred embodiment, some of said reservoirs 6 are precharged with said reagents prior to carrying out the method, even days or months before carrying out the latter, so as to have specific ready-to-use reservoirs 6. In this embodiment, the only manual step required by the operator is precharging the biological sample in said one or more reservoirs 7.

In a further preferred embodiment, in addition to said step of charging the biological sample, a further manual step performed by the operator is charging one or more drugs in one or more of said reservoirs 6.

In a preferred embodiment, said reservoirs 6, 7, integrated or external to said open reversed microwell system, pre-loaded with the reagents and the biological sample, are introduced into said automated system. In this embodiment, said charging steps d) and e) through said input ports, also referred to as input regions (8), take place following said step c) of introducing in the automated system said open reserved microwell system in which said reservoirs 7 are integrated, or said open reversed microwell system and said reservoirs 6, 7 external thereto, preferably by automated pick up of the biological sample from said reservoirs (7) and consequent arrangement of the cells contained therein in one or more of said microwells (2) and optionally, subsequent introduction of drugs in one or more of said microwells and/or dyes, and/or one or more labeled antibodies, and/or one or more cell viability markers, wherein said dyes, and/or one or more labeled antibodies and7or cell viability markers are fed to said input ports (8) from said reservoirs (6).

Said morphological/functional classification derives from the fluorescence analysis with resolution of a single cell, a single cell aggregate or the entire cell population which is contained in a single microwell.

Said parameters are acquired and analyzed automatically, through the use of systems known to those skilled in the art.

By morphological parameters it is meant measures relating to the size and shape of the cell. By functional parameters it is meant those features observed due to the markers, such as the expression of specific antigens.

In a preferred embodiment, said method also comprises, after introducing said open reversed microwell system into said automated system:

f) Filling at least one said microchannel 3 with filling buffer;

g) Acquiring images from one or more of said microwells (2), either individually or by subgroups, wherein said images are defined baseline images (T baseline);

and, in said classification step p), said classification is made with morphological and/or functional parameters detected by the comparison of images T0 with said baseline images.

Even more preferably, said method further comprises:

k) Dispensing one or more of said drugs, individually or in combination, wherein said drugs are preferably picked up in an automated manner from said reservoirs 6 and dispensed in one or more of said microwells 2;

l) Incubation.

In said embodiment, said method allows, for example, the ex-vivo analysis of the drug activity, where the classification of said cells present in said biological sample carried out in said step p) allows a direct comparison between, for example, the responsiveness to treatment of healthy cells and cancer cells present in the same biological sample, or a comparison of the response of the same cell type to different treatments.

In an even more preferred embodiment, said method further comprises, after said step l):

m) Acquiring at least two images from said one or more microwells 2, at different times during said incubation, wherein said images are defined images T1, T2, Tn, wherein n is any number equal to or greater than 2, preferably 1,000 or 100, even more preferably 25, in a preferred embodiment is 9;

n) Optionally, between said acquisitions of said images T1, T2, Tn, further dyeing said cells with one or more dyes and/or one or more labeled antibodies and or one or more cell viability markers;

o) Optionally, between said acquisitions of said images T1, T2, Tn, further dispensing of one or more of said drugs in a microwell 2 or in one or more subgroups of microwells 2, individually or in combination;

and said classification of step p) comprises the comparison of morphological and/or functional parameters detected from images T0, T1, Tn and optionally Tbaseline.

Even more preferably, said method further comprises, after said classification step p):

q) Analysis of the cell viability, where said analysis is cell-specific, or is carried out at the level of cell aggregate, or takes into account the whole cell population contained in one of said microwells 2.

In a preferred embodiment, in said step k) said drugs are dispensed in at least two different concentrations and said cellular viability analysis, when present, leads to obtaining a specific cell dose/response curve for the one or more drugs tested.

Optionally, the dilutions of each drug are prepared by the liquid dispensing system by mixing the drug with a diluent.

In a further embodiment, the method involves, after said image acquisition of step j), the count of the average number of cells in each microwell 2 and the subsequent dilution of the sample, through said fluid dispensing system, so as to achieve a target concentration, i.e. a concentration which ensures the desired number of cells per each microwell, and the subsequent charging of the sample thus diluted into one or more microchannels of said open reversed microwell system, which microchannels are different from the one or more channels used in step d) above.

In said step k), if the combined administration of at least two drugs is required, said two or more drugs are optionally combined by a liquid dispensing system by mixing, prior to charging, the content of at least two reservoirs 6 containing said drugs.

Said method is characterized in that it uses a biological sample whose volume ranges from 1 µl to 1 ml, preferably from 10 µl to 100 µl, with a cell concentration of between 5,000 cells per ml and 5,000,000 cells per ml.

In a preferred embodiment, said filling buffer comprises RPMI medium supplemented with bovine fetal serum (FBS) 10%, and preferably a cell death marker, typically propidium iodide (PI) 5 µM.

Figure 5:
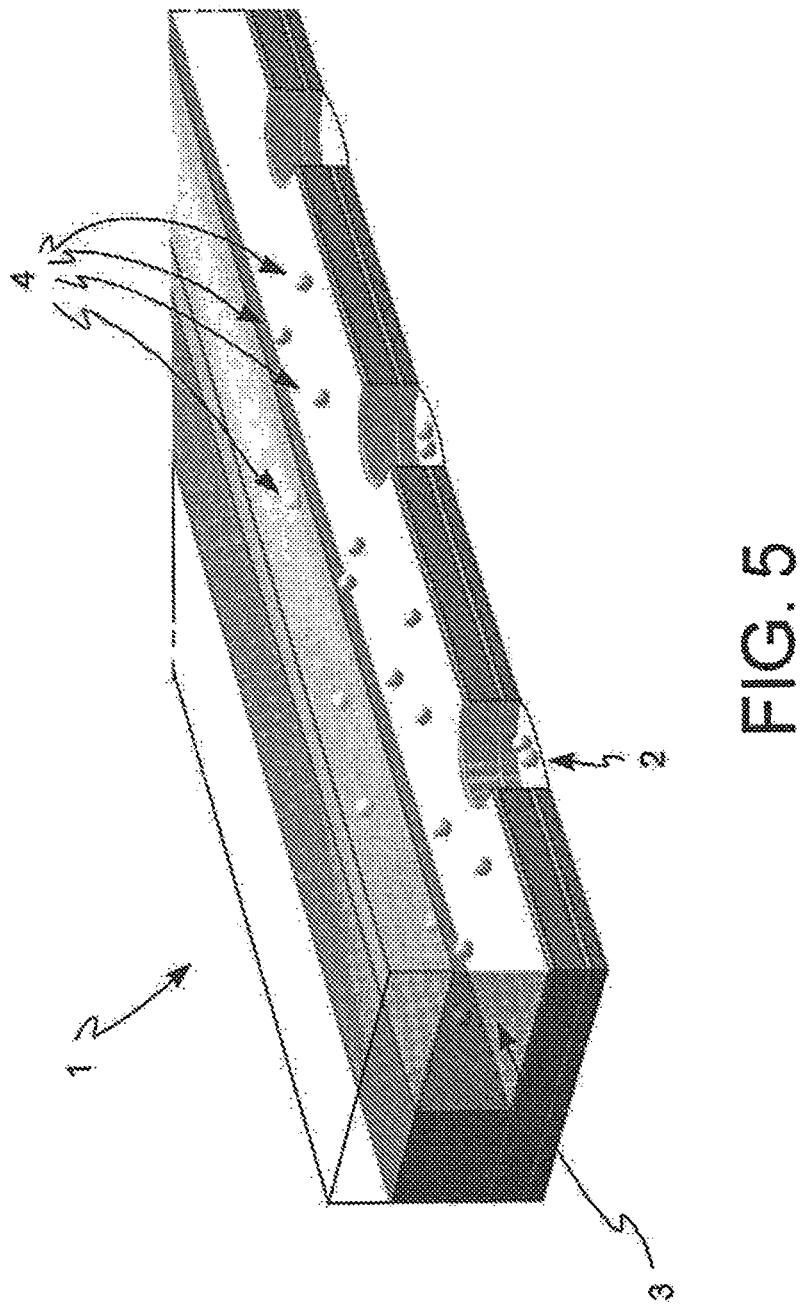
FIG. 5: sectional view of a portion of an open reversed microwell system used in the method of the present invention.

Said open reversed microwell system 1, of which FIG. 1 shows a perspective (a), vertical section (b) and top (c) view and FIG. 5 shows a perspective sectional view, in a preferred embodiment comprises 1200 microwells 2 per each microchannel 3 and 16 microchannels 3; in a further embodiment, it comprises 500 microwells 2 and 5 microchannels 3.

In a preferred embodiment, said method analyzes a biological sample which contains only about 10-20 cells and uses the open reversed microwell system of the type described in WO2012/072822.

In a preferred embodiment, said biological sample is obtained from an animal and/or a human suffering from cancer and said biological sample comprises healthy cells and cancer cells.

All the cells will be highlighted in the images acquired in phase contrast and/or, if these cells are stained with a dye, in a fluorescence channel, such as DAPI if the dye is CMAC (7-amino-4-chloromethylcoumarin). Others dyes which can be used in the method can be selected from the group comprising: Calcein-AM, carbocianine such as DiD, DiO, DAPI (4',6-diamidino-2-phenylindole). Other dyes which can be used for the purposes of the present method are cell death markers, such as PI, Calcein-AM, JC1, Caspase 3/7, Annexin V. In a further embodiment, labeled antibody are used as dyes.

In a particularly preferred embodiment, said method comprises a reiteration of the treatment, where the cells which survive a first exposure to one or more of said drugs listed in step k), are exposed again to a further drug treatment, where said further treatment involves the exposure to one or more of said drugs already used in said step k) at higher concentration, or where, in said further step, one or more drugs other than those used in the previous step are used.

The reiteration of the method takes place, in one embodiment, on the cells which remain alive in said one or more microwells 2, where said further extra treatment made possible since, in said open reversed microwell system, said microchannel 3 is emptied of said fluid comprising one or more drugs and subsequently filled with a second fluid comprising said further one or more drugs. The cells, by remaining positioned on the meniscus at the air/fluid interface, are not affected by the fluid change in said microchannel. Said cells located on the meniscus, even if they are not cells growing in adhesion, from a fluidic point of view behave like cells growing in adhesion on the bottom of a closed well, where it is typically possible to replace the culture medium without affecting said cells in adhesion. The advantage of the present embodiment is to be found in its use also with cells which grow in suspension, where said meniscus allows to mimic the bottom of a well without imposing a forced adhesion on said cells, such as using substrates which stimulate cell adhesion known to those skilled in the art. This is particularly advantageous as it allows the least impact on the biological sample, preventing imposing of external conditions alien to the physiological context.

In a preferred embodiment, said method comprises the following steps, in this order:

a) Providing a reversed open microwell system (1) which includes an array of open microwells (2), at least one microchannel (3), at least one input port (8) for reagents and/or one or more biological samples and at least one output port (10) for them, said input and output ports being in microfluidic communication with one or more of said microchannels wherein said microchannel (3) has a cross-section area of micrometric dimensions and provides fluid to said microwells (2);

b) Providing an automated management system of said reversed open microwell system which comprises the following features: incubator at controlled temperature, humidity and $CO_2$, fluid dispensing system, phase-contrast and fluorescence image acquisition;

c) Placing said reversed open microwell system (1) in said automated system;

f) Optionally filling at least one said microchannel (3) with filling buffer;

g) Optionally acquiring images from one or more of said microwells (2), either individually or by subgroups, wherein said images are defined baseline images;

d) Charging reagents through one or more of said input ports (8), where said reagents comprise: filling buffer and/or washing solution and/or one or more drugs and/or one or more dyes, and/or one or more labeled antibodies and or one or more cell viability markers and wherein said reagents are contained in reservoirs for (6) reagents;

e) Loading said one or more biological samples through one or more of those said input ports (8), wherein said one or more biological samples are contained in biological sample reservoirs (7);

i) Optionally, dyeing said cells with one or more dyes and/or one or more labeled antibodies and or one or more cell viability markers;

j) Acquiring images from one or more of said microwells (2), wherein said images are defined images T0;

k) Dispensing one or more of said drugs, through said ports (8), in one or more of said microwells (2);

l) Incubation;

m) Acquiring at least two images from said one or more microwells (2), at different times during said incubation, wherein said images are defined images T1, T2, Tn, wherein n is any number equal to or greater than 2, preferably 1,000 or 100, even more preferably 25, in a preferred embodiment is 9;

n) Optionally, between said acquisitions of said images T1, T2, Tn, further dyeing said cells with one or more dyes and/or one or more labeled antibodies and or one or more cell viability markers;

o) Optionally, between said acquisitions of said images T1, T2, Tn, further dispensing of one or more of said drugs in a microwell (2) or in one or more subgroups of microwells (2), individually or in combination;

p) Classifying the cells displayed, wherein said classification is made with morphological and/or functional parameters detected from the images T1, T1, Tn and, optionally, Tbaseline.

Cancer cells are identified by dimensional and shape parameters, such as membrane roughness, and by the bonding with labeled antibody specific for tumor antigens, where the presence or absence of a specific signal emitted by one or more specific labeled antibodies determines the identification of the cell type. By way of example, if the tumor under investigation is a lymphoma, an anti-CD38 antibody is used for the differential analysis of tumor cells; if the tumor under investigation is acute myeloid leukemia (AML), an anti-CD34, or anti-CD117, or anti-HLA-DR, or anti-CD33/CD14 antibody is used.

In a preferred embodiment, the drugs tested are selected from monoclonal antibodies, for example Alemtuzumab, Bevacizumab, Cetuximab, Tbritumomab, Ofatumumab, Panitumumab, Rituximab, Tositumomab, Trastuzumab, chemotherapy drugs, such as cytarabine, idarubicin, fludarabine, decitabine, 5-azacitidine and small molecules, such as ibrutinib, idasanutlin, venetoclax, wherein the method of the present invention measures the complement-mediated cytolytic activity, in the case of monoclonal antibodies, or the direct cytotoxic activity, in the case of chemotherapy drugs and small molecules.

The automated analysis of images obtained using the method of the present invention allows to extract the information related to each individual cell or cluster of cells, captured in the acquired images.

At the end of said method, the cells contained in the microwells may be collected and used for subsequent analysis. In particular, the method described herein allows to select one or more wells in which cells of particular interest are contained, such as drug-resistant cells injected into a specific microchannel, recharging said cells into reservoir (7) of a further open reversed microwell system, dispensing them to a greater dilution to obtain microwells containing a single cell. Once the desired cell has been identified, it can be isolated. Assays are conducted on said one or more isolated cells as known to those skilled in the art, such as RT-PCR.

The biological sample can be charged or collected/explanted, or it can be processed in advance so as to make it available in the method according to the present invention. In particular, when it is a sample of blood or bone marrow, said processing preferably involves a red blood cell separation step with techniques known to those skilled in the art, preferably on a density gradient, or through the use of a lysis buffer. When said sample comprises suspension cells, said cells are counted and diluted to the dispensing concentration. Alternatively, said count and dilution step is done automatically by the system. If the sample is a biopsy, said processing typically comprises isolating a fragment sized between 10 μm and 1000 μm, a size compatible with the microfluidics used.

In an alternative embodiment, said biological sample is used as is as an isolate from animal and/or human.

Figure 6:
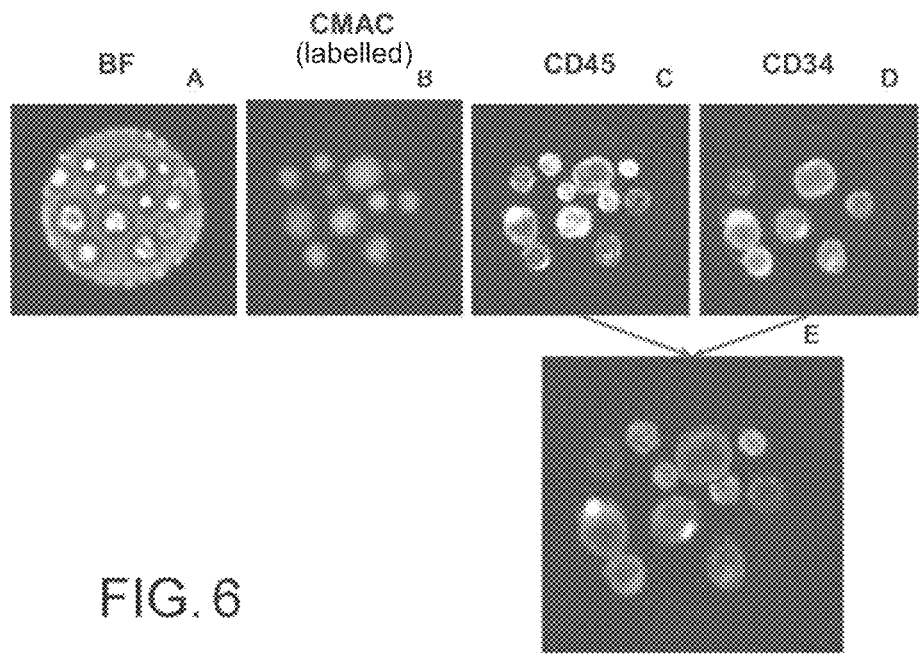
FIG. 6: example of images taken in the visible (A), in the DAPI fluorescent channel (B), in the FITC fluorescent channel (C) and in the CY5 fluorescent channel (D). (E) is the result of the superimposition of the images acquired in the FITC and the CY5 channel.
Figure 7:
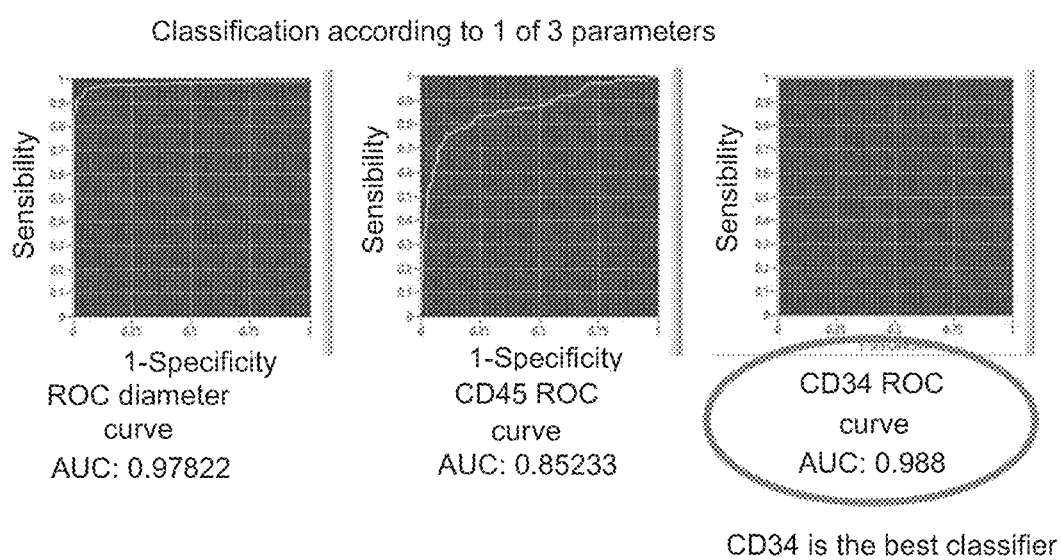
FIG. 7: classification of cell population in FIG. 6 according to the different parameters evaluated.

FIG. 6 shows an example of a series of images taken at time T1 in a biological sample consisting of leukemic cells from a cell line mixed with blood obtained from a healthy donor. The biological sample therefore contains healthy PBMC and cancer cells. The image is obtained in the risible (A) API fluorescent channel with a dye (B), in the FITC fluorescent channel for the labeled anti-CD45 antibody signal (C) and in the fluorescent channel CY5 for the labeled anti-CD34 antibody (D). Finally, (B) shows the overlap of said images (C) and (D). The method has been demonstrated to have a high sensitivity and a high specificity when applied to cell classification, as evidenced by image (B) in which all the cells present in the sample are found, namely those of the image in (B), where all cells are CD45 positive (C) only and only a part thereof is also CD34 positive (D). By analyzing the cells by morphological (cell diameter) and functional parameters (expression of CD45, CD34), a correct classification is obtained for almost ail said tumor cells, as shown in FIG. 7, which clearly shows that marker CD34 is the parameter which allows to identify the tumor cells with a high sensitivity and specificity, as is apparent from the ROC curve, for which an area under the curve is obtained being equal to 99.8% of the cells which actually are (CD34 ROC curve). Parameter CD45 instead produces an area under the curve equal to 85.2%, thus demonstrating lower sensitivity and specificity. This experiment shows that, for the tumor type being investigated, CD34 is the marker of choice and enables an extremely accurate analysis of the cell population.

Figure 8:
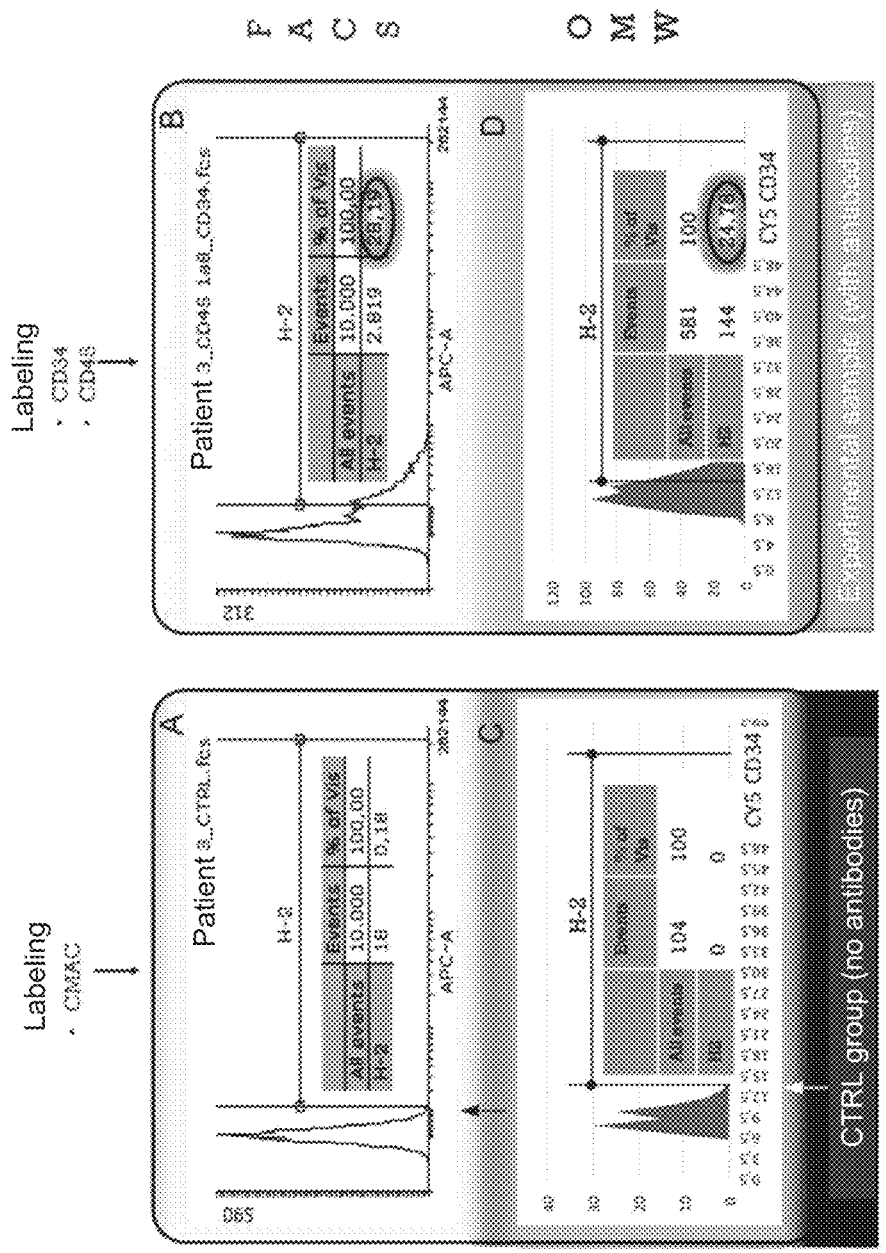
FIG. 8: classification of cancer cells in a sample of bone marrow extracted from patient affected by acute myeloid leukemia (AML). In (A) and (B), the results obtained at the FACS, in (C) and (D) the results obtained according to the method described in the present application. In (A) and (C) the baseline reading, carried out on non-labeled control cells, which allows to define a threshold value, indicated by the arrow; in (B) and (D) the counting of anti-CD34 antibody positive cells, or of events above the defined threshold value.

FIG. 8 shows the graphs of the acquired data analysis, in relation to the classification of cancer cells. (C) shows the distribution of the cells stained with dye CMAC and not stained with anti-CD34/CD45 antibodies. This distribution allows to determine the maximum signal identified in such negative control, and as a result to set a minimum threshold for the classification. Subsequently, in (D), the count made after anti-CD34/CD45 labeling was carried out keeping the threshold identified at (C) and classifying the cells characterized by a signal emitted by the antibody higher than the threshold as cancer cells. In particular, the cancer cells can be classified as such as they are positive to the anti-CD34 antibody (CD34+) and as they are positive to both anti-CD34 and anti-CD45 antibodies (CD34+/CD45+). As a control of the method, panels (A) and (B) show the results obtained by flow cytometry on the same samples. These results show that the data obtained with the method of the present invention are absolutely comparable with those obtained for the same sample by flow cytometry, which is the technique of choice for this type of analysis and cell counting.

Wanting to monitor the cell viability, in said step i) said cells are stained with cell viability markers. As an example, propidium iodide (PI) or Annexin V are commonly used markers in this regard: if the membrane is damaged, PI enters the cells and emits fluorescence after binding to nucleic acids. The labeled cells are therefore those with compromised or destroyed membrane and should be considered as dead. Another commonly used cell viability marker is calcein-acetoxymethyl (calcein-AM) (Lichtenfels R et al., CARE-LASS calcein-release-assay, an improved fluorescence-based test system to measure cytotoxic T lymphocyte activity. J Immunol. Methods 1994, 172:227-239). Calcein-acetoxymethyl ester crosses the cell membrane passively and, once inside, it is converted by an intracellular esterase into calcein, which a polar fluorescent product retained into the viable cells but released by cells whose membrane is damaged and therefore considered death.

Figure 9:
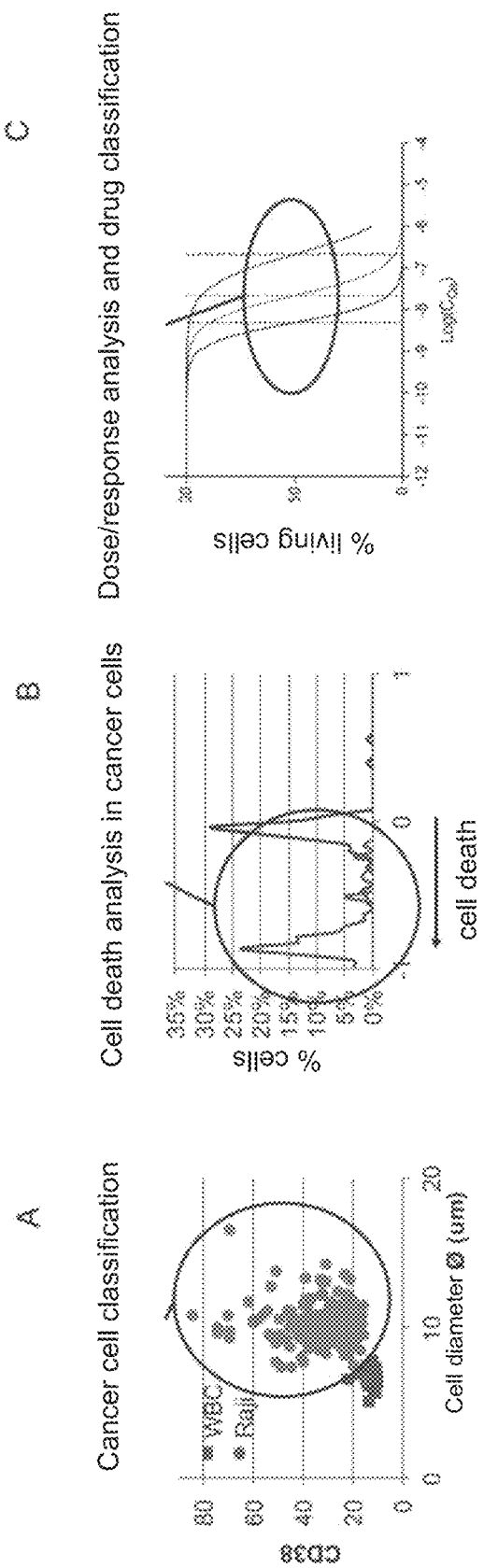
FIG. 9: data obtained on a mixture of cells extracted from a healthy donor and Burkitt lymphoma cell line (Raji) according to the method described in the present application. Classification of tumor cells in a mixture of cells extracted from healthy donor and tumor cells (A), analysis of cell death in the tumor population and in the healthy one (B) and dose/response curve after drug exposure (C).

FIGS. 9A-9B shows an example of an analysis carried out on a biological sample which includes lymphoma cell line Raji cells, and white blood cells. In the samples investigated, a treatment with a drug, specifically Rituximab, was performed according to the method of the present invention. Panel (A) shows the ability of the method according to the presence t of invention to differentiate between cancer cells (circle) and healthy cells (square), using morphological parameters and the CD38 marker simultaneously. (B) shows the cell viability data, obtained by quantifying the presence of calcein-AM in the cell, in particular by comparing the signal emitted after treatment with the drug with the signal emitted initially, where the signal reduction is associated with the loss of viability. In this case, the reference threshold is determined using a control consisting of a channel in which the sample is not exposed to the drug. Alternatively, known references in the literature concerning the physiological loss of signal are used (Neri S et al., Calcein-Acetoyxmethyl Cytotoxicity Assay: Standardization of a Method Allowing Additional Analyses on Recovered Effector Cells and Supernatants. Clin. Diagn. Lab. Immunol. 2001, 8:1131-1135).

FIG. 9C shows the dose/response curves obtained for a different model consisting of leukemic cell lines (KG-1, Kasumi-1 and HL-60) for which a response analysis to the chemotherapy drug idarubicin was carried out. The results show 3 different response levels, observable, for example, by the different IC50 values measurable indicated with the dashed vertical lines: sensitive (IC50=0.0049 μM), sensitive on the average (IC50=0.0218 μM) and resistant (IC50=0.2127 μM).

As an example, a biological sample resulting from the explantation of a liver cancer can be used in the present method, after partial non-enzymatic breakdown. The biological sample is then labeled and charged in said reservoirs. In less than one hour from the explantation, an open reversed microwell system is available which is ready for analysis, comprising cell clusters and isolated cells. The possibility of assessing the effect of drugs also on cell clusters is very advantageous, as it also allows to assess any changes in volume of the same cluster, in addition to different labeling areas in the same cluster. It is also possible to acquire images on different, focal planes, in this way being able to also reconstruct a 3D image of the cluster.

Figure 10:
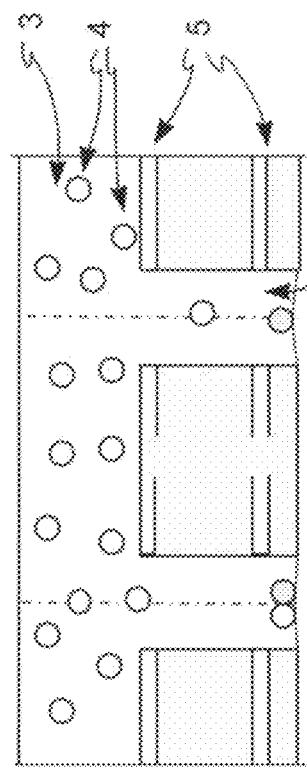
FIG. 10: schematic sectional representation of an open reversed microwell system used in an alternative embodiment of the method according to the present description, which also includes electrodes in the microwell and on the lower surface of the channel.

FIG. 10 shows the diagram of an open reserved microwell system which also comprises electrodes 5 arranged around said microwells 2 and on the base of said microchannel 3. Said electrodes 5 have the function of conveying cells 4 present into microchannel 3 into microwell 2 in the desired time and mode. The electrodes thus promote the formation of cell clusters within the microwells, thus allowing therefore an analysis which also takes into account the specific cell: cell interactions.

Advantages

The method described herein facilitates a personalized medicine approach, which is strongly needed especially when intervening in tumor diseases. In fact, the method described herein surprisingly allows testing on a biological sample ex-vivo, even comprising a few cells only, such as only about 10-20 cells, if the open reversed microwell system used in said method is of the type described in WO2012/072822, the effect of different drugs so as to allow the choice of the most effective drug for the specific patient and/or the optimal dose for the specific patient and/or the determination of the resistance of the patient sample to one or more drug therapies. The analysis is performed immediately after collection of the biological sample and is completed over a period of about 24 hours. Quick timing allows the cells within the biological sample not to undergo significant variations of their functionality, viability and gene expression, with reference to the ex-vivo features thereof. The speed with which data is obtained allows to use the same technique in clinical situations for which it is necessary to take decisions quickly, such as acute leukemias.

Moreover, considering the small biological sample needed, said method is applied without having a substantial impact on the operational procedure, as it does not require dedicated withdrawals. For example, if blood is used, a volume smaller than 1 mL is typically sufficient. In case of bone marrow, volumes equal to 1 mL are typically sufficient to run multiple tests, i.e. 0.1 mL or less to run a single test. A sample from needle aspiration can offer enough material.

The method developed herein allows the use of complex samples, including cellular and serum samples, with enormous advantages from the point of view of conditions as close as possible to the physiological ones, to improve the predictive value of the assay.

The method described herein allows a high-content analysis, with resolution up to a single cell, performing both a dynamic analysis (time-lapse) and a dynamic processing of the sample (using a programmable change of the fluids surrounding the sample over time), which are highly coveted features as they allow to monitor and compare the evolution over time of a given cell with specific features, automate the sample preparation and the administration of drugs, and implement complex protocols involving, for example, the inclusion of sequences of drugs or the labeling with specific reagents, such as Annexin V, at the end of the incubation period with the drug for determining the outcome of the experiment in terms of viability, induction of apoptosis or assessment of the activation of specific pathways associated with the activity of the drug.

Among the many applications for which the method described herein is particularly functional we may mention the possibility of comparing, in a quick and automated manner, the responsiveness of a patient's cancer cells to a specific treatment and the average responsiveness of cancer cells of a population of patients affected by the same type of tumor. Moreover, there is the possibility of comparing the responsiveness of cancer cells of a patient to a specific treatment with the average responsiveness of cell lines relating to the same type of tumor and/or to different tumor types, such as referring to literature data.

The process fully automated, the operator's intervention is minimum, i.e. only when charging the biological samples and reagents and drugs into the reservoirs. In some embodiments, the intervention is exclusively limited to the charging of the biological sample, when the open reversed microwell system comprises reservoirs already charged with reagents and drugs, minimizing thus errors, reducing the risk of cross-contamination and significantly increasing the reproducibility of the results. It is also possible to charge the biological sample as it is, with no preparation: the system itself is able to detect the number of cells contained therein, dilute them to the optimal dilution and dispense them in the microwells of interest.

In the embodiment comprising electrodes into the microwells, it is possible to obtain specific groupings of cells into individual microwells, so as to assess cell-dependent mechanisms of action.

As a further advantage, it is noted herein that by working on a micrometric scale, the consumption of reagents and drugs is also limited, for example the drugs are diluted into volumes of just 20-50 microliters, with considerable saving with respect to the requirements when working on larger volume, a particularly apparent advantage when the drugs used are very expensive, or in the step of developing the drug, when the availability thereof may be limited, especially in the case of biological drugs.

In a particularly preferred embodiment, a method for the large-scale high-content analysis of biological samples is described, comprising the following steps, not necessarily in this order:
a) Providing a kit according to claim 9 or 10;
b) Providing an automated management system of said reversed open microwell system which comprises the following features: incubator at controlled temperature, humidity and $CO_2$, fluid dispensing system, phase-contrast and fluorescence image acquisition;
c) Placing said reversed open microwell system (1) in said automated system;
d) Charging reagents through one or more of said input ports (8), where said reagents comprise: filling buffer and/or washing solution and/or one or more drugs and/or one or more dyes, and/or one or more labeled antibodies and or one or more cell viability markers;
e) loading said one or more biological samples through one or more of said input ports (8);

Optionally, dyeing said cells with one or more dyes and/or one or more labeled antibodies and or one or more cell viability markers;
Acquiring images from one or more of said microwells (2), wherein said images are defined images T0;
Classifying the cells displayed, wherein said classification is made with morphological and/or functional parameters detected from the images T0.

EXAMPLE 1

Assessing the Effectiveness of Rituximab on Non-Hodgkin Lymphoma Cells

Cells: SU-DHL-4 lymphoma cells and Raji cells were used (ATCC CCL-86). $3·10^5$ cells/mL were cultured in RPMI medium supplemented with 10% FBS, 1% puromycin/streptomycin at 37° C., 95% RH, 5% $CO_2$. The cells were amplified, dividing them when in confluence. PBMC were isolated from blood by centrifugation in gradient. Whole blood from healthy donors was collected into tubes treated with anticoagulants according to the directive "ethical principles and guidelines for the protection of humans in research". Isolated PBMC were washed twice with 10 mL cold HBSS after lysis of red blood cells. The concentration of cells and their viability was determined with Trypan Blue on haemocytometer. The concentration was adjusted to 1 million cells/mL.

Different batches of SU-DHL-4 or Raji cells were harvested at the peak of their growth, washed with PBS and counted in a hemocytometer with Trypan Blue. The cell concentration was adjusted to 1 million cells/mL and they were labeled with Calcein AM (CAM) 5 nM for flow cytometry and 250 nM for the assay according to the present invention. The labeled cells were washed once in PBS and resuspended in RPMI. The same protocol was used to label with freshly isolated CAM PBMC. Cell viability was finally assessed by PI and flow cytometry.

Flow Cytometry (Comparative)

$10^5$ CAM labeled cells for each batch were seeded in duplicate on a 96 well plate. The control group (CTRL) was treated with RPMI supplemented with PI to a final concentration of 1.5 µM. The treatment group was treated with Rituximab (RTX) to a final concentration of 10 µg/mL in RPMI supplemented with PI to a final concentration of 1.5 µM and incubated at room temperature for 5 min. Soon after, human serum (hS) was added to a final concentration of 1%. The final volume of each well was 200 µL. 50 µL samples were harvested at time 0, 30 and 60 min. after adding hS, and analyzed at the FACS (FACSAria BD, USA).

Open Well Assay

Different batches of CAM labeled cells were resuspended in RPMI to a final concentration of $2·10^6$/mL. Similarly to the procedure followed for flow cytometry, the RIX group was treated with Rituximab to a final concentration of 10 µg/mL off-chip and incubated at room temperature for 5 min. CTRL and RTX cells were seeded in the open reversed microwell system as described, obtaining an optimum number equal to or smaller than 7 cells per well. The channels were rinsed with PBS on 20% FBS. A first set or images was acquired to set the initial conditions (Tbaseline). After charging, the CTRL channel was treated with RPMI integrated with hS to a final concentration of 1% and PI at a concentration of 5 µM. The RTX channel was treated with RPMI supplemented with Rituximab 10 µg/mL, HS 1% and PI 5 µM. Time-lapse images T1, T2, T3, T4 were acquired every 15' and up to one hour after treatment.

Microscopy

The images were acquired brightfield (BF) to evaluate the morphological characteristics and then in fluorescence to evaluate the signal in DAPI bands (ex: 360/40 nm, 460/50 nm), FITC (ex: 480/30 nm, em: 535/40 nm), TRITC (ex: 540/25 nm, em: 605/55 nm). All images were acquired with 10× lens with a Nikon camera. During the imaging, the microscope worked in a controlled atmosphere at 37° C., 95% humidity, 5% $CO_2$.

Display

SU-DHL-4 cancer cells were labeled with CAM and then charged into the open microwell system, treated with drug in the case of the RTX group and observed.

Figure 11:
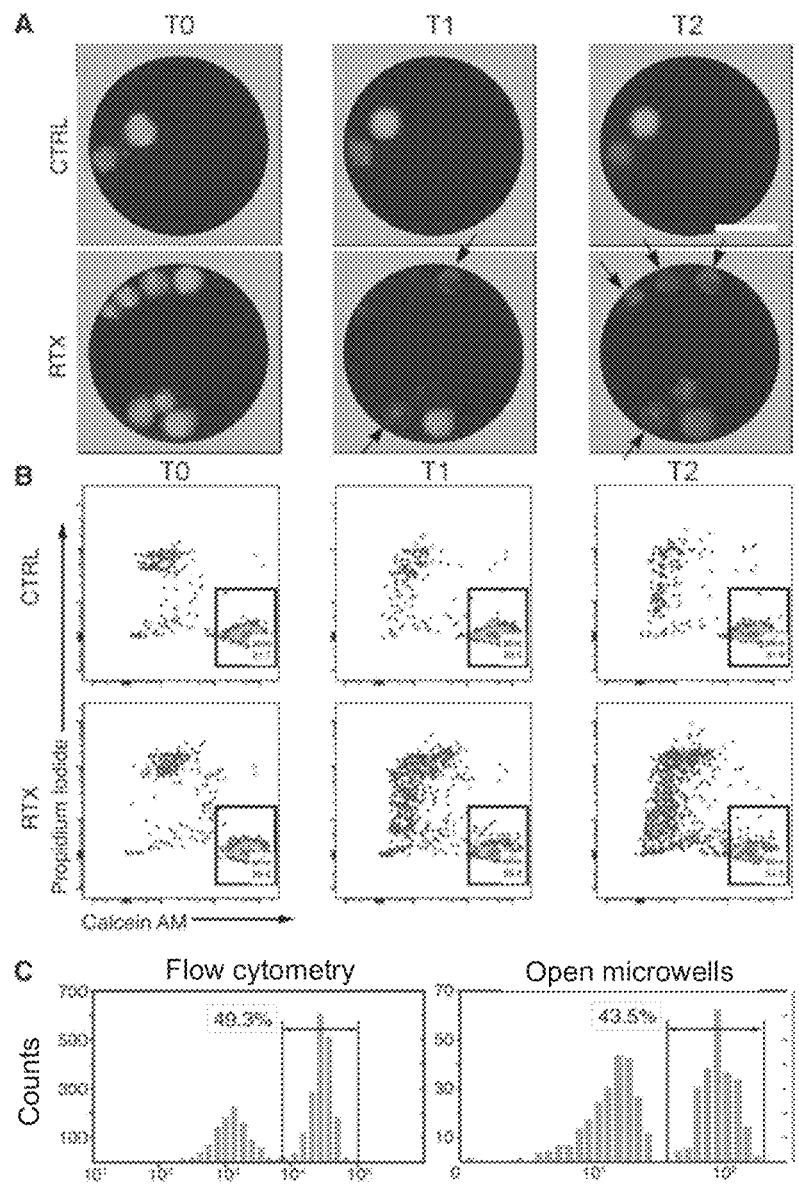
FIG. 11: assay on SU-DHL-4 (RTX) treated and untreated (CTRL) tumor cells with the monoclonal antibody Rituximab. (A) observation of living cells (light gray) and dead cells (indicated by the arrow) at time zero (T0), and after 30 (T1) and 60 (T2) minutes of treatment using the method according to the present invention; (B) count of live cells at T0, T1 and T2 obtained by flow cytometry; (C) comparison between the cell count data obtained after 60 minutes of treatment by flow cytometry or using the method according to the present invention.
Figure 12:
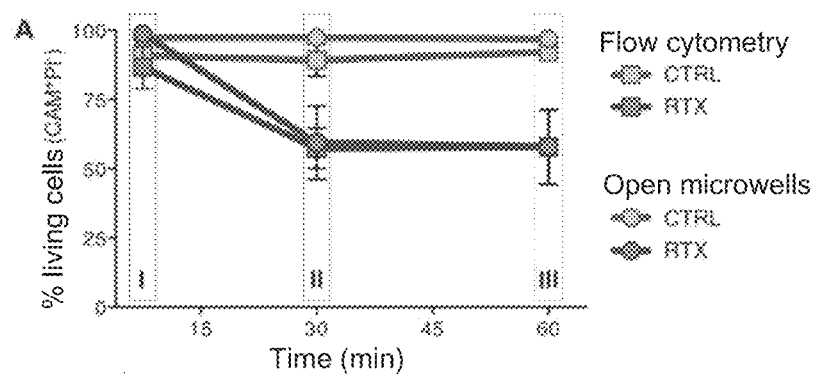
FIG. 12: cell count indicated as a percentage of SU-DHL-4 tumor cells survived after treatment, obtained by FACS (squares) and using the method according to the present invention (circle) in control cells (light gray) and treated with Rituximab (dark gray).

The results are shown in FIG. 11. Panel A shows a sequence of time-lapse images of CTRL and RIX treated samples at times T0 5-10 min, T1 30 min and T3 60 min. The cells indicated by the arrows refer to the color acquired in the TRITC channel (PI) and represent dead cells. They are present only at T2 and T3 in the RTX group. With greater contrast, the cells acquired in the FITC channel are seen, i.e. live cells labeled with Calcein-AM. Panel B shows the data obtained with the FACS. Panel C shows the histograms of FACS analysis and according to the method of the present invention at time T2 60 minutes. The percentages refer to the population of Calcein-AM positive cells, i.e. living cells. As can be seen, the data obtained with the two methods are totally comparable. As a confirmation, the data are presented in a linear manner in FIG. 12, leading to the conclusion that the system according to the present invention can be used to quantify living and dead cells over time, providing data equivalent to what is now the technique of choice, i.e. flow cytometry, with all the advantages of the high-content analysis possibilities not possible with flow cytometry.

Figure 13:
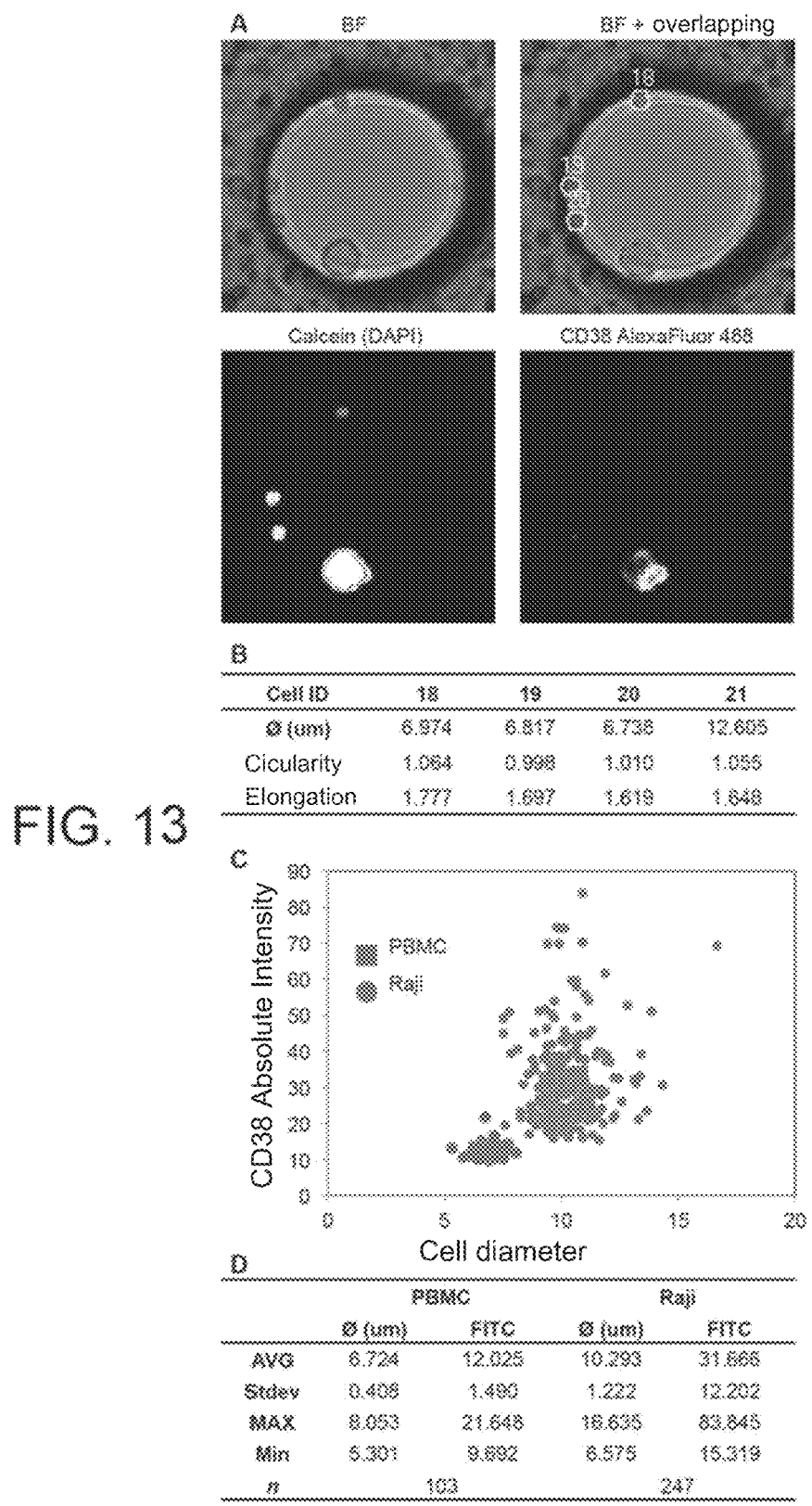
FIG. 13: classification of Raji tumor cells within a mixture of cells extracted from healthy donor and said Raji tumor cells using the method according to the present invention. (A) phase-contrast and fluorescence observation; (B) cell-specific morphological data; (C) classification of cells considering morphological (diameter) and functional (CD38 expression) parameters; (D) statistical analysis of morphological (diameter) and functional (CD38 expression) data from a population of healthy cells (peripheral blood mononuclear cells, PBMC) and tumor cells (Raji).

The method according to the present invention further proves to be able to provide important results, not obtainable with flow cytometry. First, it was observed that the mixture of Raji cancer cells and PMBC it was possible, thanks to the CD38 labeling, to stain and selectively observe cancer cells. To this end, Raji cancer cells and PBMC were labeled with CAM and with an anti-CD38 antibody Alexa Fluor 488 1:10, separately. A portion of the cells was then mixed in a 1:1 ratio. Raji cells, PMBC and the mixture were then plated in three different channels of the open reversed microwell system and then observed. As shown in FIG. 13, cancer cells, highlighted in A for the selective staining with the anti-CD38 antibody with respect to the total cells stained with CAM, are easily highlighted by the method of the present invention not only for the fluorescence associated with the specific marker (panel C) but also for the morphological parameters (panel B and D)

The acquisition of images in time-lapse has the advantage of providing an accurate analysis of every cellular response to stimuli represented, for example, by drug treatment, where the precise analysis is obtained by evaluating the relative variation of fluorescence which, in case of staining with a vital dye, provides a means to determine the cellular response. Even where the initial staining is not uniform, the signal from each cell is then normalized to its initial value. In comparison, the absolute fluorescence analysis after the application of a treatment, as typically provided by flow cytometry, provides a less accurate result in this case.

Figure 14:
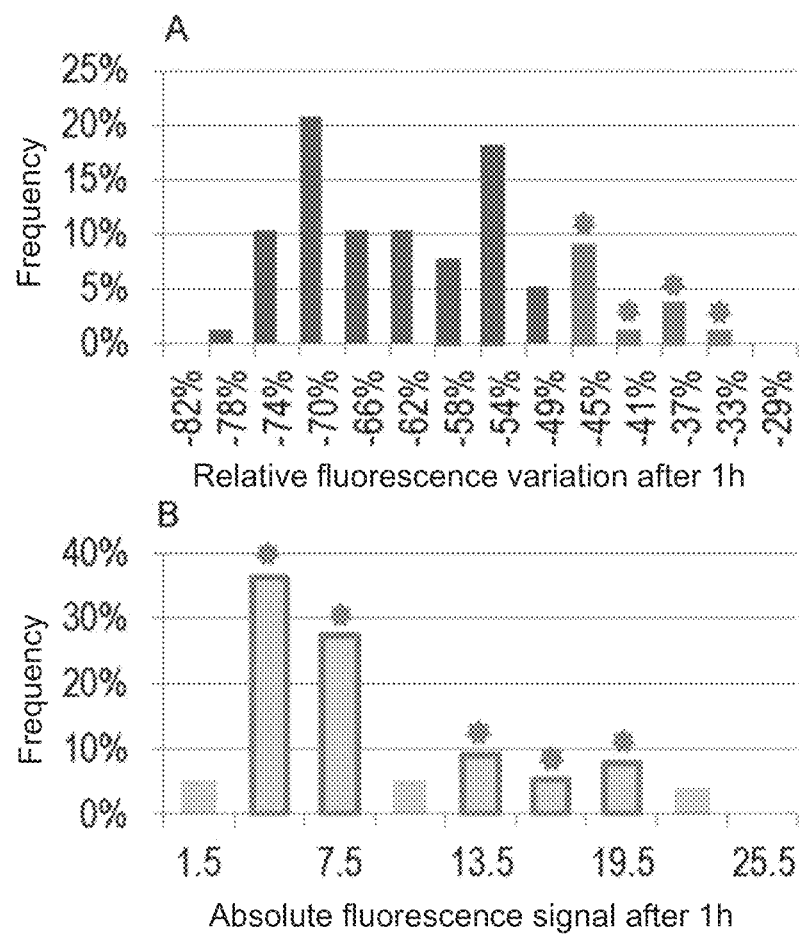
FIG. 14: Changes in the fluorescence signal over time Data obtained in time-lapse in cell-specific mode (A) or as total observation of the cell population (B). In the figure (A), histogram columns are highlighted, corresponding to the subpopulation which has suffered the least cell damage, which is the lowest relative variation of the fluorescent signal. The figure (B) shows the columns corresponding to subpopulations which contain the same cells identified in the graph (A).

For example, FIG. 14 compares the distribution obtained by dynamic analysis, i.e. variation of relative fluorescence in A, versus the distribution of the data obtained in absolute terms, in B. The first distribution in FIG. 14A was obtained according to the method described herein on Raji cells after exposure to Rituximab. The cells showing a reduced signal intensity variation represent a subpopulation of possibly resistant cells, or which underwent minor damage. By using this distribution, cells for which the variation was less than a 45% decrease were selected, indicated with a star (*) in the figure, and they were analyzed within an analysis showing the variation in absolute terms (FIG. 14B). In particular, in this figure the columns marked with a star indicate the presence of at least one cell identified as resistant from the previous analysis. As shown in FIG. 14B, absolute analysis does not provide a means to identify cells with a low damage with the same accuracy as the method shown in FIG. 14A, as evidenced by the fact that there is a column on the left side of the histogram which shows a subset of cells with minimum absolute intensity but which are not classified as resistant according to relative analysis, in fact, the column is not marked by any star. Likewise, on the right side of the graph there are cells which despite having a high signal intensity showed a significant signal loss and, therefore, should be considered as sensitive to therapy according to the relative analysis.

EXAMPLE 2

Automated Labeling Process, Analysis in Time-Lapse

Figure 15:
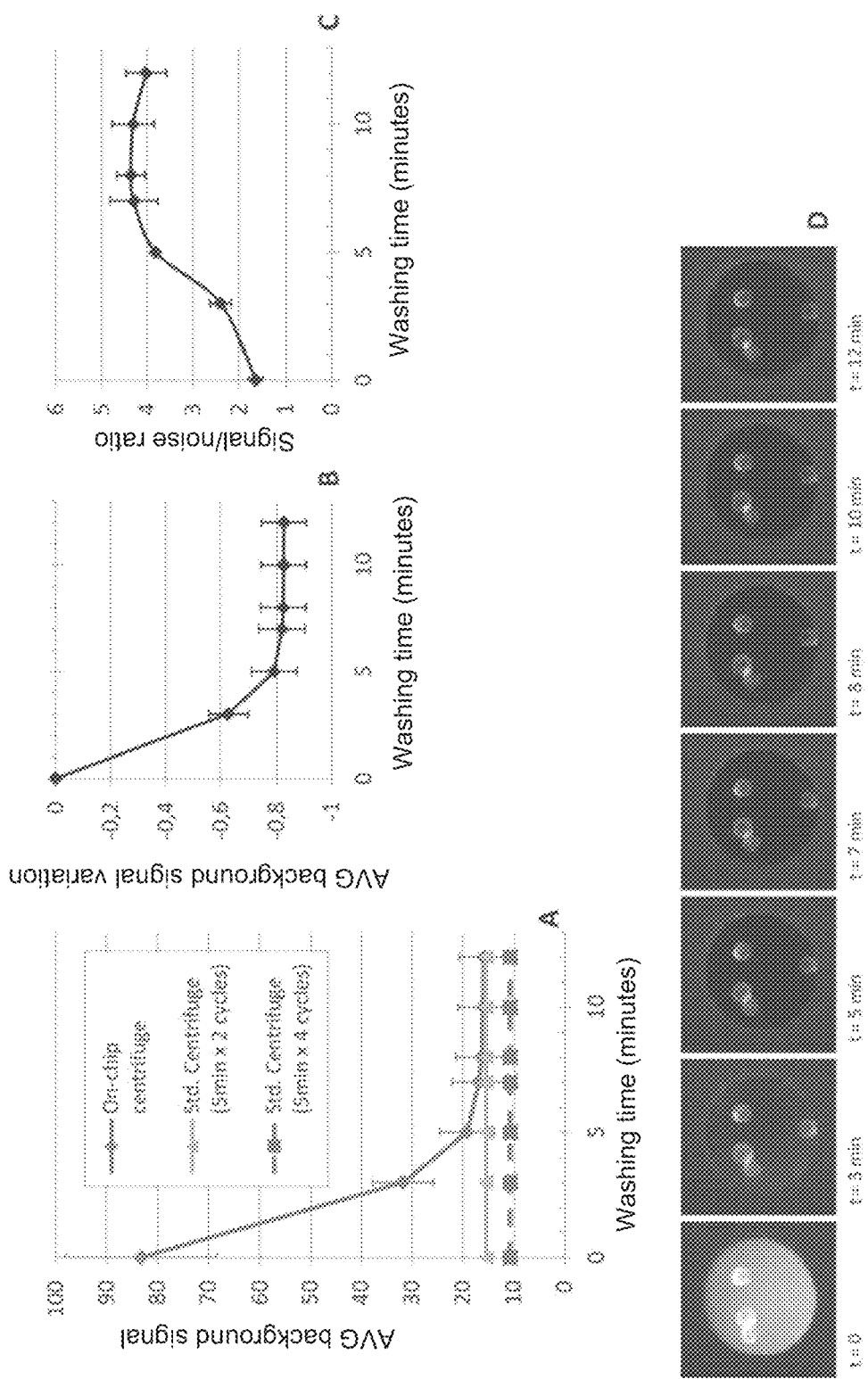
FIG. 15: automated labeling process. (A) shows the background signal and (B) the variation of said signal over time, as measured in a microwell by operating at a 16 µL/minute flow rate. The dotted line in (A) represents the background signal which measured not operating in time-lapse but alternating measurements and washing. (C) shows the signal/background noise ratio, expressed as the average signal measured on cells divided by the average background signal. (D) shows representative pictures of the image collection in time-lapse during washing.

Cells are loaded into microwells 2 of an open reversed microwell system. The medium in which such cells were contained is then eliminated with a series of repeated washings, where such washings take place by passing through said microchannels 3 a washing fluid, such as HBSS. Images are acquired at subsequent times during said washing operations and panel C in FIG. 15 shows images acquired at time 0 and after 3, 5, 7, 8, 10 and 12 minutes from the washing. In the graphs shown in panels B and C in the same FIG. 15, the curves indicate the reduction of background noise which is obtained by using said washings. In panel A, the procedure according to the method described herein is compared with a standard method, which requires subsequent centrifuging. In particular, the uninterrupted line marked by the rhombus indicates the result over time with the method according to the present invention, where a decrease of 79.1% of the background noise is observable after 5 minutes of continuous infusion of the washing solution at a rate of 16 μL/minute. The dashed line represents the result obtained through the standard centrifugation process, where the result obtained after 4 washing cycles separated by 5 minutes centrifuge at 1000 RCF is shown. The uninterrupted line marked by the triangle shows the result obtained after 2 cycles separated by 5 minutes centrifuge at 1000 RCF. The method according to the present invention allows to obtain comparable results, with the obvious advantage of not requiring lengthy centrifugation which inevitably leads to loss of biological material, which loss in some situations may be significant to a point susceptible to compromise the analysis itself, as well as an exposure of the biological sample to additional stress.

EXAMPLE 3

Evaluation of the Efficacy of OKT3 On Lymphoblasts T

Cells from the Jurkat cell line (human Leukemic T cells) were obtained from ATCC and cultured in RPMI 1640 medium supplemented with 10% inactivated FBS medium, 10 mM Hepes, 2 mM Ultraglutamine and 1 mM sodium pyruvate, 1% Penicillin/Streptomycin in 25 cm$^2$ flasks at 37° C. and 5% $CO_2$.

The OKT3 hybridomas were cultured in bioreactors (Cell-Line, Integra Biosciences) in complete RPMI 1640 medium containing 3% FBS and the supernatant was collected 2 times a week. The purification of monoclonal antibodies was performed using a double saturated ammonium sulfate precipitation at 30% and 50%, followed by dialysis in PBS. The purity of OKT3 was assessed by SDS-PAGE gel and the amount of antibody was determined through NanoDrop (Thermo Scientific). The antibody was then frozen at −80° C. before use.

For comparison, the measure of calcium signal on entire populations of Jurkat cells was performed following the protocol Fluo-4 (Life Technologies). 1×10$^6$ Jurkat cells were washed once in HBSS and incubated with Fluo-4 (4 ng/µL) for 30 minutes at 37° C. After washing and resuspension in HBSS, the cells are treated with the purified antibody OKT3 at the concentrations of 1, 5 and 10 µg/mL or, alternatively, using 50 µL of supernatant from hybridoma culture. As a positive control of the calcium flow, Ionomycin (Sigma-Aldrich) 2 µg/mL was added. The cells thus treated were then analyzed at the flow cytometer.

For the assay in open microwells according to the present invention, Jurkat cells were labeled with Fluo-4 20 µM in HBSS, centrifuged and resuspended in serum-free medium (RPMI 1640 with 25 mM Hepes or HBSS) at a concentration of 1.6×10$^6$ cells/mL in 1.5 mL Eppendorf tubes used as input reservoirs for the open reversed microwell system. Subsequent to the deposition of Jurkat cells in the microwells (approximately 1-10 cells per microwell) and washing the channels with HBSS, the solutions containing Ionomycin (2 µg/mL) or OKT3 (10 µg/mL) are made to flow into specific microchannels of the open microwell system via peristaltic pump. The images were acquired by a camera connected to the microscope at a distance of 1 minute and processed by software developed in LabView, quantifying the dynamic performance of the same signal on each sample cell.

Figure 16:
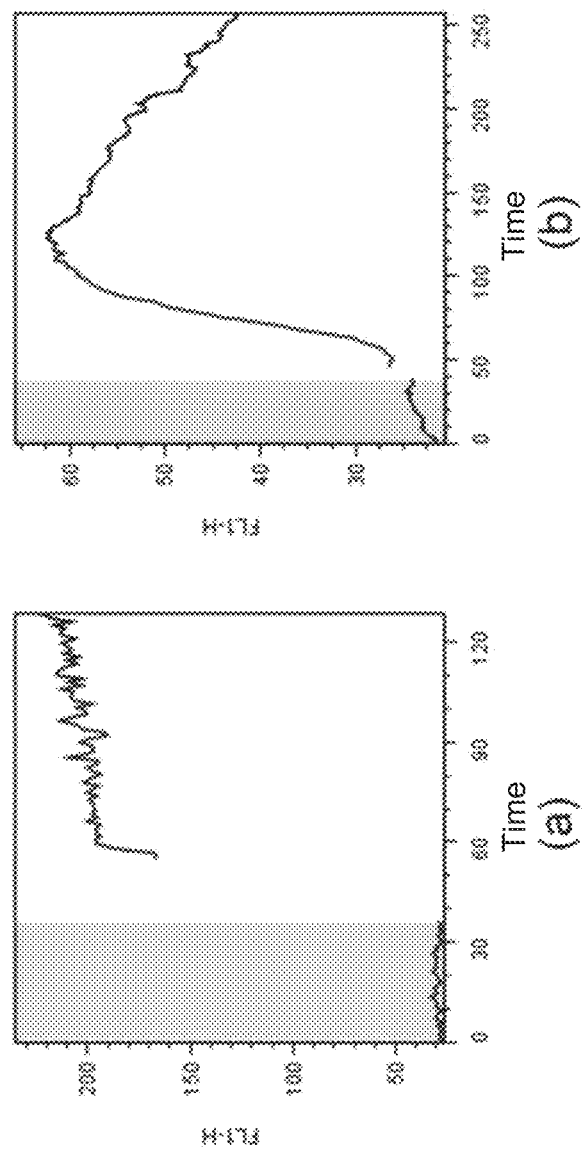
FIG. 16: Temporal analysis by flow cytometry of the signal variation at a wavelength of 480 nm (FITC) by Jurkat cells labeled with Fluo-4 as a result of stimulation with (a) Ionomycin and (b) purified antibody OKT3.

Cytofluorimetric results: the progress of the average sample fluorescence following the injection of Ionomycin (a) or OKT3 (b) in the sample was quantified at flow cytometer, obtaining the results shown in FIG. 16. The charts show the average variation of the fluorescence intensity and confirm the functioning of the model used.

Background signal variation in open microwells: the variation of the signal emitted by the single cells labeled with Fluo-4 in the absence of stimulation was quantified after charging the cells in the open microwell system. The analysis showed an increase of the signal equal to 38%.

Figure 17:
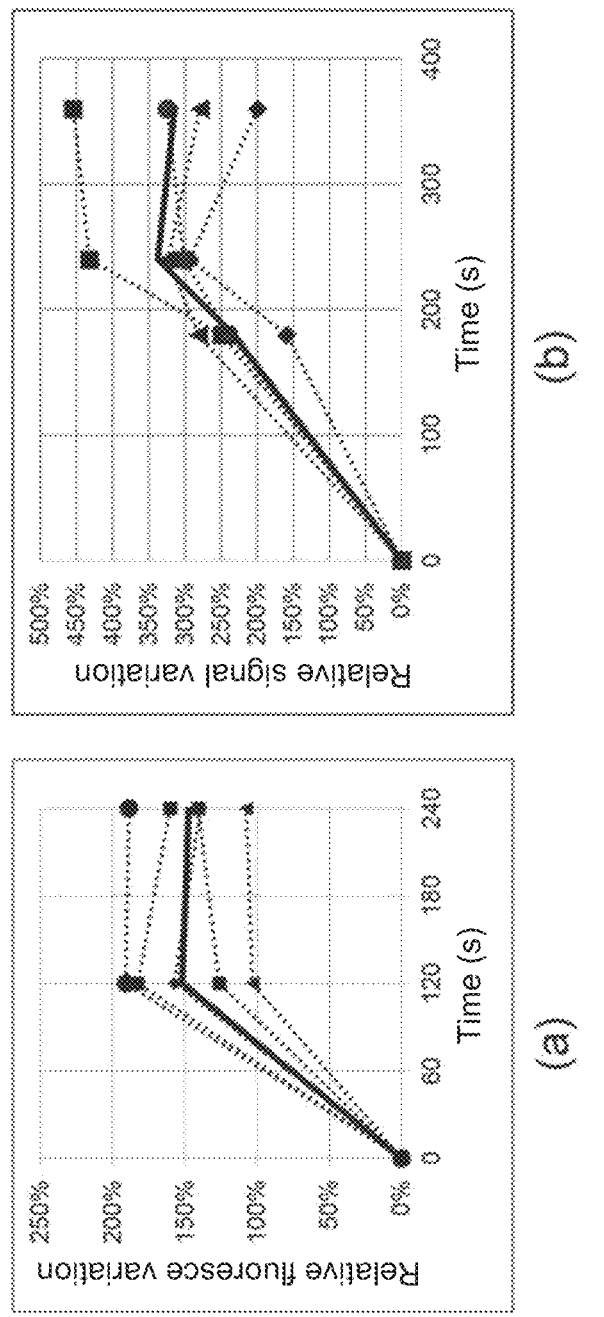
FIG. 17: Temporal analysis in the open microwell system of the signal variation at a wavelength of 480 nm (FITC) by Jurkat cells labeled with Fluo-4 as a result of stimulation with (a) Ionomycin and (b) purified antibody OKT3. The dashed curves represent the signal sequence obtained for individual cells in the microwells. The continuous curve represents the mean value of the signal.

Ionomycin stimulation in open microwells: the stimulation with Ionomycin showed an average increase of the signal, with respect to the baseline, equal to 193%+/−139% an a series of 10 experiments. The typical pattern observed is that shown in FIG. 17(*a*). As observed also at the flow cytometer, in case of Ionomycin stimulation, following an initial increase of fluorescence, the signal settles on stably high values.

The stimulation with OKT3 showed an increase of the signal peak, compared to the baseline value, equal on an average to 178%+/−90% in a series of 3 experiments. The typical pattern observed is that shown in FIG. 17(*b*). As observed also at the flow cytometer, in case of OKT3 stimulation, following an initial increase of fluorescence, the signal reached the peak value in a few minutes.

The comparative experiment shows that the method according to the present invention allows to have data comparable to those obtained with the method of choice, i.e. flow cytometry.

The invention claimed is:

1. A method for charging/discharging fluids from a microfluidic device, wherein said method comprises:
    a) providing a kit comprising:
    a tip;
    a microfluidic device comprising a reversed open microwell system, the reversed open microwell system comprising an array of open microwells, at least one microchannel, at least one input port for at least one reagent and/or for one or more biological samples, and at least one output port for the at least one reagent and/or one or more biological samples, said input and output ports being in microfluidic communication with one or more of said at least one microchannels, wherein said at least one microchannel has a cross-section area of micrometric dimensions and is configured to provide a fluid to microwells of said array of open microwells;
    a discharge region which comprises: an unloading container in fluid connection with said microfluidic device by means of at least one unloading channel and one outlet door, wherein said unloading channel emerges from said at least one microchannel and is a siphon;
    wherein said tip comprises a proximal portion intended to cooperate with a fluid dispensing system and a distal portion, said proximal portion of generally tubular configuration and said distal portion is open tapered wherein the terminal base of said distal portion is made of plastic has an outer diameter of dimension d3, and the upper base of said distal portion has an outer diameter of dimension d4, wherein a distance between said upper base and said terminal base of said distal portion is h2, the half-opening of a truncated cone formed by said distal portion is (90°-β), and said proximal portion has a height of h3; wherein said input port comprises a plastic vertical channel leading into said at least one microchannel, an upward opening of said vertical channel having a diameter of d2, where d3<d2, said vertical channel is a channel tapered downwards having an upper base and a lower base, said lower base having a diameter of dimension d1, said vertical channel having a height h1 and a half-opening of the truncated cone formed by said tapered channel being (90°-α1); said tip and said vertical channel being dimensioned so as to produce an interference coupling therebetween; wherein said microfluidic device is charged with at least a first fluid; and
    b) exerting a pressure on said at least a first fluid entering said microfluidic device; or
    c) arranging a discharge region wherein said discharge channel has a diameter such as to make said fluid pass from said microfluidic device to said discharge channel by capillarity;
    wherein a volume V of said at least a first fluid is smaller than or equal to the volume of said discharge container, and said at least first fluid reaches said discharge container in a unidirectional manner.

2. The method for charging/discharging fluids according to claim 1, wherein said method further comprises:
    introducing a second or further fluid through said input port in said microfluidic device, wherein said first, second and/or further fluids are independently equal or different from one another and are selected from the group comprising liquids and gases; and said second and/or further fluid completely replaces in said microchannel or in said microchannel and in said reversed open microwells, when present in said microfluidic device, the fluid introduced before;

wherein said first, second and/or further fluids do not mix with one another.

3. A method for the large-scale high-content analysis of biological samples, comprising the following steps:

providing a kit comprising:

a tip;

a microfluidic device comprising a reversed open microwell system, the reversed open microwell system comprising an array of open microwells, at least one microchannel, at least one input port for at least one reagent and/or for one or more biological samples, and at least one output port for the at least one reagent and/or one or more biological samples, said input and output ports being in microfluidic communication with one or more of said at least one microchannels, wherein said at least one microchannel has a cross-section area of micrometric dimensions and is configured to provide a fluid to microwells of said array of open microwells;

a discharge region which comprises: an unloading container in fluid connection with said microfluidic device by means of at least one unloading channel and one outlet door wherein said unloading channel emerges from said at least one microchannel and is a siphon;

wherein said tip comprises a proximal portion intended to cooperate with a fluid dispensing system and a distal portion, said proximal portion of generally tubular configuration and said distal portion is open tapered wherein the terminal base of said distal portion is made of plastic has an outer diameter of dimension $d3$, and the upper base of said distal portion has an outer diameter of dimension $d4$, wherein a distance between said upper base and said terminal base of said distal portion is $h2$, the half-opening of a truncated cone formed by said distal portion is $(90°β)$, and said proximal portion has a height of $h3$; wherein said input port comprises a plastic vertical channel leading into said at least one microchannel, an upward opening of said vertical channel having a diameter of $d2$, where $d3<d2$, said vertical channel is a channel tapered downwards having an upper base and a lower base, said lower base having a diameter of dimension $d1$, said vertical channel having a height $h1$ and a half-opening of the truncated cone formed by said tapered channel being $(90°-α1)$; said tip and said vertical channel being dimensioned so as to produce an interference coupling therebetween;

providing an automated management system of said reversed open microwell system, the automated management system comprising the features of: an incubator at controlled temperature, humidity and CO2 level, a fluid dispensing system, and phase-contrast and fluorescence image acquisition;

placing said reversed open microwell system in said automated system;

charging reagents through one or more of said input ports, wherein said reagents comprise at least one of: filling buffer, washing solution, one or more drugs, one or more dyes, one or more labeled antibodies, and one or more cell viability markers;

charging said one or more biological samples through one or more of said input ports;

acquiring images from one or more of said microwells, wherein said images are defined images T0; and classifying the cells displayed, wherein said classification is made with morphological and/or functional parameters detected from the images T0.

4. The high-content analysis method according to claim 3, further comprising, after the introduction of said reversed open microwell system in said automated system: filling at least one said microchannel with filling buffer; and acquiring images from one or more of said microwells, either individually or by subgroups, wherein said images are defined baseline images; wherein said classification is made with morphological and/or functional parameters detected by the comparison of images T0 with said baseline images.

5. The high-content analysis method according to claim 3, wherein said biological sample comprises about 10-20 cells.

6. The high-content analysis method according to claim 3 wherein, at the end of said method, the surviving cells are harvested and used in subsequent analyses.

7. The high-content analysis high-content analysis method according to claim 3, wherein said method further comprises: charging a fluid into said tip; positioning said tip above said input port and inserting it into said input port to reach an interference coupling position between said distal region of said tip and said vertical channel in said input port; releasing the fluid contained in said tip in said microfluidic device through said input port or, with the same tip, suctioning fluid already contained in said microfluidic device.

8. The high-content analysis method according to claim 7, wherein said microfluidic device of said kit further comprises a discharge region which comprises: a discharge container in fluidic connection with said microfluidic device through at least one discharge channel and an output port, and said method further comprises forcing said fluid, pushed by a pressure applied in said input port in said microfluidic device, unidirectionally into said discharge container, where a volume V of said fluid is smaller than or equal to the volume of said discharge container.

9. The high-content analysis method according to claim 3, further comprising dyeing said cells with at least one of: one or more dyes, one or more labeled antibodies, and one or more cell viability markers.

* * * * *